United States Patent [19]
Herrmann et al.

[11] Patent Number: 6,165,993
[45] Date of Patent: Dec. 26, 2000

[54] DNA VACCINES AGAINST ROTAVIRUS INFECTIONS

[75] Inventors: John E. Herrmann, Northborough; Harriet L. Robinson, Southborough; Ellen F. Fynan, Sterling, all of Mass.

[73] Assignee: University of Massachusetts Medical Center, Worcester, Mass.

[21] Appl. No.: 09/233,813

[22] Filed: Mar. 2, 1998

Related U.S. Application Data

[63] Continuation of application No. 08/842,563, Apr. 15, 1997, abandoned, which is a continuation of application No. 08/426,169, Apr. 20, 1995, Pat. No. 5,620,896, which is a continuation-in-part of application No. 08/187,879, Jan. 27, 1994, which is a continuation-in-part of application No. 08/009,833, Jan. 27, 1993, Pat. No. 5,643,578, which is a continuation-in-part of application No. 07/855,562, Mar. 23, 1992, abandoned.

[51] Int. Cl.$^7$ ..................... A61K 31/7052; C12N 15/63; C12N 15/88
[52] U.S. Cl. .................. 514/44; 536/23.1; 536/23.4; 435/320.1
[58] Field of Search ............................ 435/320.1, 235.1; 514/44; 424/93.2; 536/23.1, 23.5, 23.4

[56] References Cited

U.S. PATENT DOCUMENTS

| | | | |
|---|---|---|---|
| 4,722,848 | 2/1988 | Paoletti et al. | 424/199.1 |
| 5,620,896 | 4/1997 | Herrmann et al. | 435/320.1 |
| 5,827,696 | 10/1998 | Estes | 435/91.41 |

FOREIGN PATENT DOCUMENTS

| | | |
|---|---|---|
| 029879A3 | 11/1988 | European Pat. Off. . |
| 2166349A | 5/1986 | United Kingdom . |
| WO 86/00930 | 2/1986 | WIPO . |
| WO 86/07593 | 12/1986 | WIPO . |
| WO 90/02797 | 3/1990 | WIPO . |
| WO 90/02803 | 3/1990 | WIPO . |
| WO 90/11092 | 10/1990 | WIPO . |
| WO 92/01045 | 1/1992 | WIPO . |
| WO 92/07941 | 5/1992 | WIPO . |
| WO 95/20660 | 8/1995 | WIPO . |

OTHER PUBLICATIONS

Chattergoon et al. Genetic Immunization: A New Era in Vaccines and Immune Therapeutics. FASEB, vol. 11, pp. 753–763, Aug. 1997.
McDonnell et al. Molecular Medicine DNA Vaccines. The New England Journal of Medicine, vol. 334, pp. 42–45, Jan. 4, 1996.
Gorziglia et al. Similarity of the Outer Capsid Protein VP4 of the Gottfried Strain of Porcine Rotavirus to that of Asymptomatic Human Rotavirus Strains. Journal of Virology, vol. 64, pp. 414–418, Jan. 1990.
Barry, Michael A., et al., *BioTechniques*, 16(4):616–619 (1994).
Both, G.W., et al., *Virology*, 193:940–950 (1993).
Brown, W. David, et al., *Avian Diseases*, 36:515–520 (1992).
Chapman, B.S., et al., *Nucleic Acids Research*, 19:3979–3986 (1991).
Cheng, L., et al., *Proc. Natl. Acad. Sci USA*, 90:4455–4459 (1993).
Cichutek, K., *Vaccine*, 12(16):1520–1525 (1994).
Cohen, J., *Science*, 259:1691–1692 (1993).
Conner, M.E., et al., *Current Topics in Microbiology and Immunology*, 185:285–337 (1994).
Cox, Graham J.M., et al., *Journal of Virology*, 67(9):5664–5667 (1993).
Cullen, B.R., *Cell*, 46:973–982 (1986).
Davis, H.C., et al., *Vaccine*, 12(16):1503–1509 (1994).
Davis, H.L., et al., *Human Gene Therapy*, 4:151–159 (1993).
Davis, H.L., et al., *Human Molecular Genetics*, 2(11):1847–1851 (1993).
Davis, H.L., et al., *Human Gene Therapy*, 4:733–740 (1993).
Dharakul, T., et al., *Journal of Virology*, 65(1):5928–5932 (1991).
Donnelly, J.J., et al., *Journal of Immunological Methods*, 176:145–152 (1994).
Dormitzer, P., et al., *IXth Intl. Congress of Virology*, Workshop W21 (1993).
Dormitzer, P., et al., *Abstr. IXth Intl. Congress of Virology*, W21-2, p. 43 (1993).
Dunn, S.J., et al., *Virology*, 203:250–269 (1994).
Eisenbraun, Michael D., et al., *DNA and Cell Biology*, 12(9):791–797 (1993).
Estes, M.K., et al., *Microbiol. Rev.*, 53:410–449 (1989).
Estes, M.K., et al., *Strategies for Pediatric Vaccines*, 149–156 (1994).
Franco, M., et al., *Journal of Virology*, 69(12):7800–7806 (1995).
Fynan, E.F., et al., *Proc. Natl. Acad. Sci. USA*, 90:11478–11482 (1993).
Fynan, E.F., et al., *DNA And Cell Biology*, 12(9):785–789 (1993).
Hunt, Lawrence A., et al., *Journal of Virology*, 62(8):3014–3019 (1988).
Huylebroeck, et al., *Technological Advances in Vaccine Development*, 84:279–293 (1988).

(List continued on next page.)

*Primary Examiner*—Deborah J. R. Clark
*Attorney, Agent, or Firm*—Fish & Richardson P.C.

[57] ABSTRACT

This invention relates to methods of eliciting an immune response and/or protective immunity in a vertebrate by introducing into the vertebrate a DNA vaccine which consists essentially of DNA encoding an antigen or antigens, e.g., capsid proteins or polypeptides, of rotavirus. The uptake of the DNA vaccine by a host vertebrate results in the expression of the capsid protein, thereby eliciting humoral or cell-mediated immune responses, or both, which can provide protection against infection and/or prevent clinically significant rotavirus-caused disease. In addition, the invention demonstrates that an internal viral antigen provides protective immunity in a host. The host can be any vertebrate, including birds, piglets, and humans.

17 Claims, 18 Drawing Sheets

OTHER PUBLICATIONS

Katsumi, A., et al., *Human Gene Therapy*, 5:1335–1339 (1994).
King, *Biotechnology News*, 11(28):5 (1991).
Liu, M.A., et al., abstracts of papers presented at the 1992 meeting on Modern Approaches to New Vaccines Including Prevention of AIDS, Cold Spring Harbor Laboratory, New York, Sep. 16–Sep. 30, 1992.
Montgomery, Donna L., et al., *DNA and Cell Biology*, 12(9):777–783 (1993).
Nishikawa, K., et al., *Nucl. Acids Res.*, 16:11847 (1988).
Palombo, et al., "Sequences of VP6 genes of human rotavirus strain RV3 and its vaccine derivative," *Journal of General Virology*, 75:2415–2419 (1994).
Parker, S.E. et al., "Intramuscalus Vaccination of Plasmid . . . A Letal Viral Challenge", Modern Approaches to Vaccines including Prevention of AIDS, Cold Spring Harbor Laboratory, New York Sep. 16–Sep. 20, 1992.
Paul, et al., "Immunogens of rotaviruses," *Veterinary Microbiology*, 37:299–317 (1993).
Rhodes, Gary H. et al., "Injection of Expression . . . Immunity to the Antigen", presented at 1992 meeting on Modern Approaches to Vaccine, Cold Spring Harbor Laboratory, New York, Sep. 16–Sep. 20, (1992) (Abstract).
Rhodes, Gary H. et al., "A Novel Method of Inducing . . . Protein by DNA Injection", Presented at meeting on Modern Approaches to Vaccines, Cold Spring Harbor Laboratory, New York Sep. 16–Sep. 20, (1992) (Abstract).
Riepenhoff–Talty, M., et al., *Adv. Exp. Med. Biol.*, 2168:1015–1023 (1987).
Robinson, H.L., *Vaccine*, 11(9):957–960 (1993).
Tang, D., et al., *Nature*, 356:152–154 (1992).
Taniguchi, K., et al., *J. Virol.*, 62:2421–2426 (1988).
Tarlow, O., et al., *Nucl. Acids. Res.*, 18:4921 (1990).
Ulmer, Jeffrey B., et al., *Science*, 259:1745–1749 (1993).
Ulmer, J.B., et al., *Vaccine*, 12(16):1541–1544 (1994).
Wang, B., et al., Presented at 1992 meeting on Modern Approaches to New Vaccines, Including Prevention of AIDS, Cold Spring Harbor Laboratory, New York, Sep. 16–Sep. 20, (1992), (Abstract).
Wang, Ban et al., *DNA and Cell Biology*, 12(9):799–805 (1993).
Ward, R.L., et al., *J. Virol.*, 64:5070–5075 (1990).
Watanabe, Akira, et al., *The Journal of Immunology*, 151(5):2871–2876 (1993).
Webster, R.G., et al., *Vaccine*, 12(16):1495–1498 (1994).
Williams, R.S., et al., *Proc. Natl. Acad. Sci. USA*, 88:2726–2730 (1991).
Yang, N.S., et al., CRC Crit. *Rev. Biotechnol.*, 12:335–356 (1992).
Yang, N.S., et al., *Proc. Natl. Acad. Sci. USA*, 87:9568–9572 (1990).
Yankauckas, Michelle A., et al., *DNA and Cell Biology*, 12(9):771–776 (1993).
Xu, et al., "Investigation of promoter function in human and animal cells infected with human recombinant adenoviruses expressing rotavirus antigen VP7sc," *Journal of General Virology*, 76:1971–1980 (1995).
Zinkernagel, *Fundamental Immunology*, 3rd Edition, pp. 1211–1250, (1993).

Ew4
Murine Rotavirus
VP4

```
   1 ggctataaaa tggcttcact catttataga caactgctca cgaattcctt
  51 taccgtacat atatctgatg aaattgaaac tattggagca gagaagacac
 101 aaaatgttac agtgaatccc ggtccattcg cgcaaacggg atacgcccca
 151 gcaaactggg ggccaggcga aactaacgac tcaacaacag tagaaccaat
 201 gcttgatgga ccataccaac caatagcgtt cagtccgccg ccagagtact
 251 atatcatcct ctccccgact gcacccggag taatcgctga atgtacgaat
 301 actgtcaacc gctggatagc aatcatagct atagagccaa acgtgtcaac
 351 aacaaatcgt acctacacat tgttcggaat tactgaacag ctaacagtag
 401 aaaacagctc cgtggataaa tggaagttta tagacttcat gaaaactcca
 451 acaactggca gctacgtccg ttataacatt ttgttgtcta gcactaagct
 501 atgcgcagtg gcgaacgaca cggacaattt atactcctat gttggagaaa
 551 cgcctactgc aggtcaggca tactactctt ctttcaatat atttaaccta
 601 accgcgcact gtgacttcta cattatacca tggtcgcagc aatcgttgtg
 651 cacgcaatac gttaataacg gattaccgcc gatccagaat acaagaaatg
 701 tagtgccaag acatctgtca gcgagatcaa tcatcacaca aagagcgcaa
 751 cagaatgaag acattgttgt gtcaaagaca tccttatgga agaaatgca
 801 gtttaatagg gacataacaa tacgtttcaa attcgcgaat gcaataataa
 851 agtctggcgg cttgggatat aattggtcag agatctcttt caaaccagcg
 901 aactaccaat acacgtacac acgtgatggt gaagaagtaa ctgcgcatac
 951 tacgtgctcg gtaaacggtg tgaacaactt cgatttcttt ggcggtacgc
1001 tccctacgga tttcggtatt tcgcggtacg aagtgattaa ggagaattca
1051 ttcgtgtaca tagactattg ggacgactct caggctttca gaaatatggt
1101 ctatgtgcgc tcactagcgg ctgatttgaa cactgtcgaa tgcactgggg
1151 gggcgtacag cttttcacta ccagttgggc aatggccggt gatgacgggt
1201 ggtgcagtgt ctttgcgagc tgccggagtt acactatcta cacagttcac
```

FIG. 11

```
1251    agacttcgtg  tcgctaaatt  cgttgagatt  taggtttcgt  ttgtcagtgg
1301    aagaaccgtc  attcagtata  acgagaacaa  gagtgtcagg  gctatacggc
1351    ttgccagagc  gggatcctaa  caacggcaga  gaatattacg  aaattgcagg
1401    tagattttcg  ttaatatcat  tagtgccgtc  caacgataac  tatcaaacac
1451    cgataatgaa  ttcagttacg  gtgcggcaag  atctggagag  acagctaggc
1501    gaactacgac  gagaattcaa  cgcgctgtcg  caggaaatag  cgctgtcaca
1551    gttggtggat  ttagcgctac  tgccattaga  tatgttctca  atgttttcag
1601    gcatcaaagc  aacgctcgac  gtggcaaagt  caatggcaac  gaacgtgatg
1651    aaaaaattca  aaaaatcggg  actggccacg  tcgatttcac  gcatgactga
1701    gtcactatca  gatgcagctt  cctcagtgtc  tcggagtgag  ctgcatacgc
1751    tcagtcagtt  ccacgtcatc  agcttggaca  gacgtttcgt  agctgctgtg
1801    gccaacgtgg  aaaatgccgc  ctcaacagtt  tcaacacaga  cggccacaat
1851    cagcagacgg  ttgagactga  aggaaatcac  aacgcagact  gaaggcatga
1901    acttcgatga  catctcagcc  gctgtactta  aaactaagct  tgataaatca
1951    gtacgaatcg  cgccgaacac  gctaccagac  atagtaacag  aagcgtcaga
2001    gaagttcatt  ccgaacagat  catacagagt  tataaacaac  aatgaagcat
2051    tcgaaactgg  aactgacgga  cgcttcttcg  cataccgagt  tgacactctt
2101    gaggaactgc  cattcgacgt  tcagaaattc  gcatgccatg  ctgcagagtc
2151    cccagtaatc  tcagccatca  ctgacttcaa  gactttgaaa  aatttgaacg
2201    ataactacgg  aatctcgaaa  gaacaggcct  tcagtttatt  acgctcagat
2251    ccgcgagtac  tccgtgaatt  tattaatcag  gggaatccaa  taatacgtaa
2301    tagaatagaa  cagttaatta  tgcagtgtag  actgtgagca  gtgtctagag
2351    gatgtgacc (SEQ ID NO: 1)
```

FIG. 11A

Human Rotavirus
VP4

```
   1 GGCTATAAAATGGCTTCGCTCATTTATAGACAGCTTCTCACTAATTCATA
  51 TTCAGTAGATTTACATGATGAAATAGAGCAAATTGGGTCAGAAAAAACTC
 101 AAAACGTAACTGTAAATCCAGGTCCATTTGCCCAAACTAGATATGCTCCA
 151 GTAAATTGGGGTCATGGAGAGATAAATGATTCAACCACAGTAGAACCAAT
 201 TTTAGATGGTCCTTATCAGCCTACTACATTTAAACCACTTACTGATTATT
 251 GGATACTTATTAACTCAAATACAAATGGAGTGGTATACGAGAGTACGAAT
 301 AATAGTGACTTTTGGACTGCAGTAGTTGCTATTGAACCGCACGTTATCCA
 351 AGTAGATAGACAATATACTGTATTTGGTGAAAATAAACAATTTAATGTAA
 401 GAAATGATTCAGATAAATGGAAGTTTTTAGAAATGTTTAGAGGCAGTAGT
 451 CAAAATGAATTTTATAATAGACGTACACTAACTTCTGATACTAAACTCGT
 501 AGGAATATTAAAATATGGTGGAAGGATATGGACATTTCATGGTGAAACAC
 551 CGAGAGCTACTACTGATAGTTCAAATACTGCAAATTTAAACGATATATCA
 601 ATTATAATACATTCAGAATTTTATATTATCCCAAGGTCCCAAGAATCTAA
 651 GTGTAATGAATATATTAACAATGGTTTGCCACCAATTCAAAATACTAGAA
 701 ATGTAGTACCATTATCATTATCATCTAGATCCATACAGTATAAAAGAGCA
 751 CAAGTTAATGAAGATATTACAATTTCAAAAACCTCATTATGGAAAGAAAT
 801 GCAATGTAATAGGGATATTATAATTAGATTTAAATTTGGTAATAGTATTG
 851 TAAAACTGGGGGGACTAGGTTATAAATGGTCCGAAATATCATATAAAGCA
 901 GCAAATTATCAATATAATTATCTACGTGATGGCGAACAAGTAACTGCACA
 951 TACTACTTGCTCAGTAAATGGAGTAAATAATTTTAGCTACAACGGAGGAT
1001 CTTTACCTACTCATTTTAGTGTCTCAAGGTATGAAGTTATTAAAGAAAAT
1051 TCTTATGTATATGTAGATTATTGGGATGATTCAAAAGCATTTAGAAATAT
1101 GGTATATGTCAGATCATTAGCAGCTAATTTGAACTCAGTGAAATGTACAG
1151 CTCCAACTTATCACTTTAGTATACCTGTAGGTGCATGGCCAGTCATGAAT
1201 GGTGGCGCTGTTTCGTTGCATTTTGCTGGAGTTACATTATCTACGCAATT
1251 CACAGATTTCGTATCATTCAATTCACTACCATTTACATTTACTTTGACAG
1301 TGGATGAGCCATCTTTTTCAATATTGAGAACACGTACGGTGAATTTGTAC
1351 GGATTACCAGCTGCAAATCCAAATAATGGAAATGAATACTATGAAATATC
1401 AGGAAGGTTTTCGCTCATTTCTTTACTTCCAACTAATCATCATTATCACA
1451 CTCCAATTATGAATTCAGTAACAGTAAGACAAGATTTAGAACGTCAACTT
1501 ACTCATTTACCACACCAATTTAATTCATTATCACAAGAAATAGCTATGTC
1551 ACAATTAATTGATTTAGCGTTATTACCTTTAGATATGTTTTCTATGTTTT
1601 CGGAATTAAAAAGTACAATTGATTTGACTAAATCAATGGCAACTAGTGTA
1651 ATGAAAAATTTAGAAAATCAAAATTACCTACATCAATTTCAGAAATGAC
1701 TCATTCATTGTCAGACGCAGCATCATCAGCATCAAGAAGCGTTTCTATCA
1751 GATCGAATATATCCACAATTTCGAATTGGACTAATGTTTCAAATGATGTA
1801 TCAAATGTGACTAATTCGTTGAGTGATATTTCAACACAAACGTCTACAAT
1851 CAGTAAGAACCTTAGATTAAAAGAAATGATTACTCAAACTGAAGGAATGA
1901 GTTTTGATGATATTTCAGCGGCAGTATTAAAAACAAAAATACATATCTCT
1951 ACTCAAATTGGAAAGAATACTTTACCCGATATAGTCACAGAGGCATCTGA
2001 GAAATTTATTCCAAAACCATCCTATCCAATATTCAAACATGATCAACTAA
2051 TGGAAATTAATACTGAAGGGAAGTCTTTGCATATAAAATCGACACACTT
2101 AATGAAGTGCCATTTGATGTAAATAAATTTGCTGAACTTGTAACAAATTC
2151 TCCAGTTATATCAGCAATAATCGATTTTAAAACATTAAAAAATTTCAATC
2201 ATAATTATGGAATTACTCAATAGAAGCATTAAATTTAATTAAATCGAAT
2251 CCAAATGTATTACGTAATTTCATTAACCAAAATAATCCAATTATAAGGAA
2301 TAGAATTGAACAGCTAATTCTACAATGTAAATTGTGAGAACGCTATTGAG
2351 GATGTGACC (SEQ ID NO: 5)
```

FIG. 12

Human Rotavirus
VP6

```
      ----,----+----,----+----,----+----,----+----,----+----,----+
   1  GGCTTTAAAACGAAGTCTTCGACATGGAGGTTCTGTATTCATTGTCAAAA
  51  ACTCTTAAAGATGCTAGGGATAAGATTGTTGAAGGTACATTATATTCTAA
 101  TGTTAGTGATCTCATTCAGCAATTTAATCAAATGATAGTAACCATGAATG
 151  GAAATGACTTTCAAACTGGAGGAATTGGCAATTTACCTATTAGAAATTGG
 201  ACATTTGACTTTGGTCTACTAGGTACTACGCTGTTAAACCTTGATGCTAA
      ----,----+----,----+----,----+----,----+----,----+----,----+
 251  TTACGTTGAGACTGCAAGAACTACAATTAAGTATTTTATTGACTTTATTG
 301  ATAATGTATGTATGGATGAAATGGCAAGAGAGTCTCAAAGAAATGGAGTA
 351  GCTCCACAATCTGAGGCATTGAGGAAGCTAGCCGGTATTAAATTTAAAAG
 401  AATAAATTTTAATAATTCATCAGAATATATAGAAAATTGGAATTTACAAA
 451  ATAGAAGACAGCGTACCGGATTTGTTTTCCATAAACCTAATATATTTCCA
      ----,----+----,----+----,----+----,----+----,----+----,----+
 501  TACTCAGCATCATTTACTTTAAATAGGTCTCAACCAATGCATGACAATTT
 551  AATGGGAACCATGTGGCTTAACGCTGGATCAGAAATTCAAGTGGCTGGAT
 601  TTGACTACTCGTGTGCCCTAAATGCTCCAGCAAATATTCAGCAGTTTGAA
 651  CATATTGTCCAGCTTAGGCGTGCGCTAACTACAGCTACTATAACTTTGCT
 701  ACCTGATGCAGAAAGATTTAGTTTTCCAAGAGTTATTAATTCAGCAGATG
      ----,----+----,----+----,----+----,----+----,----+----,----+
 751  GCGCAACCACATGGTTCTTTAATCCAATTATCCTAAGACCAAACAATGTA
 801  GAGGTAGAATTTTTACTGAATGGACAAATTATTAATACATATCAAGCTAG
 851  ATTTGGAACTATTATCGCAAGAAATTTTGATACAATTCGTCTATCATTCC
 901  AATTAATGCGTCCACCAAACATGACGCCAGCCGTAAATGCATTATTTCCG
 951  CAAGCACAACCTTTTCAACATCATGCAACAGTTGGACTTACGTTACGTAT
      ----,----+----,----+----,----+----,----+----,----+----,----+
1001  TGAGTCTGCAGTTTGTGAATCAGTGCTTGCGGATGCAAATGAAACTTTAT
1051  TGGCGAATGTTACTGCAGTACGTCAAGAGTATGCTATAGGCGTTGGACCA
1101  GTATTTCCACCAGGCATGAATTGGACTGAGCTGATTACTAACTATTCACC
1151  ATCCAGGGAAGATAATTTGCAACGTGTCTTTACAGTAGCCTCTATCAGAA
1201  GCATGTTAATTAAGTGAGGACCAGACTAACCATCTGGTATCCAATCTTAA
      ----,----+----,----+----,----+----,----+----,----+----,----+
1251  TTAGCATGTAGCTATGTCAAGTCATTCAGACTCTACAAGTAAGGACATGA
1301  TTTCATGTTCGCTACGTAGAGTAACTGCATGAATGATCTAGTGAGAGGAT
1351  GTGACC  (SEQ ID NO: 2)
```

FIG. 13

Bovine Rotavirus
VP6

```
        ----,----+----,----+----,----+----,----+----,----+
   1   GGCTTTTAAACGAAGTCTTCAACATGGATGTCCTGTACTCCTTGTCAAAA
  51   ACTCTTAAAGATGCTAGAGACAAAATTGTCGAAGGCACATTATACTCCAA
 101   TGTAAGTGATCTAATTCAACAATTTAATCAAATGATAATTACTATGAATG
 151   GAAATGAGTTCCAAACTGGAGGAATTGGTAATCTACCGATTAGAAATTGG
 201   AATTTTGATTTTGGATTACTCGGAACAACTCTACTAAATTTGGATGCCAA
        ----,----+----,----+----,----+----,----+----,----+
 251   CTACGTCGAAACGGCCCGCAATACAATTGATTATTTTGTAGATTTTGTAG
 301   ATAATGTATGTATGGATGAAATGGTTAGAGAATCACAAAGAAATGGAATT
 351   GCACCACAATCAGATTCACTTAGAAAGTTGTCAGGTATTAAATTCAAAAG
 401   AATAAATTTTGACAATTCATCAGAATACATAGAGAACTGGAATTTGCAAA
 451   ACAGAAGACAAAGAACGGGTTTTACATTTCATAAACCAAACATTTTCCCT
        ----,----+----,----+----,----+----,----+----,----+
 501   TACTCAGCGTCATTCACACTGAACAGATCACAACCAGCTCATGATAACTT
 551   GATGGGTACGATGTGGCTCAATGCGGGATCAGAAATTCAGGTCGCTGGAT
 601   TCGATTATTCATGTGCAATCAATGCGCCAGCCAATACACAACAATTTGAG
 651   CATATTGTACAGCTCCGAAGAGTGTTGACTACAGCTACAATAACTCTTTT
 701   ACCAGATGCAGAAAGATTTAGTTTTCCAAGAGTGATTAATTCAGCTGACG
        ----,----+----,----+----,----+----,----+----,----+
 751   GAGCTACTACATGGTACTTCAACCCAGTGATTCTTAGACCAAATAACGTT
 801   GAAGTAGAGTTTCTACTAAACGGGCAGATAATAAATACTTACCAAGCAAG
 851   ATTTGGAACGATCATAGCTAGAAATTTTGATACAATTAGATTGTCATTTC
 901   AGTTGATGAGACCACCAAATATGACACCAGCGGTAGCGGCGTTATTTCCA
 951   AATGCGCAGCCATTTGAACATCAGGCAACAGTAGGACTCACGCTTAGAAT
        ----,----+----,----+----,----+----,----+----,----+
1001   TGAATCTGCAGTTTGTGAATCAGTGCTTGCCGACGCAAGTGAAACAATGC
1051   TAGCAAATGTGACATCTGTTAGACAAGAATACGCGATACCAGTTGGACCA
1101   GTTTTTCCACCAGGTATGAATTGGACTGATTTGATCACTAACTATTCACC
1151   ATCTAGAGAGGATAATTTGCAGCGTGTATTTACAGTGGCTTCCATTAGAA
1201   GCATGCTTGTCAAATGAGGACCAAGCTAACCACTTGGTATCCGACTTTGG
        ----,----+----,----+----,----+----,----+----,----+
1251   TGAGTATGTAGCTACGTCAAGCTGTTTGAACTCTGTAAGTAAGGATGCGT
1301   CTACGTATTCGCTACACAGAGTAATCACTCAGATGGCGTAGTGAGAGGAT
1351   GTGACC  (SEQ ID NO: 3)
```

Murine Rotavirus
VP7

```
GGCTTTAAAAGAGAGAATTTCCGTTTGGCTAGCGGTTAGCTCCTTTTAATGTATGGTATT 60
GAATATACCACAGCTTTAACTTTCCTGATATCATTTCTTTTATTGCGCTACATACTAAAA 120
TCAGTAGTTAAAATTATGGACTTTATAGTTTACAGGTTTTTGTTTGTAATTCTAATTTTG 180
TCGCCATGTATTAAAGCTCAAAACTACGGCATTAATCTTCCAATTACTGGTTCAATGGAC 240
ACTGCGTATGCAAACTCAACTCAACCGGAGACATTTCTGACTTCCACTCTATGCCTTTAC 300
TATCCAACAGAAGCAGCTACTGAGATAAAGGATAACTCGTGGAAAGACACGTTATCGCAA 360
CTATTCTTAACGAAAGGATGGCCAATAGGGTCAGTCTATTTTAAAGAATACACCGACATA 420
GCAGCGTTCTCAATCGATCCACAACTATACTGTGATTACAACGTAGTGCTGATGAAATAT 480
GACGCTTCATTACAAATGGATATGTCGGAACTTGCAGACTTGATACTGAATGAATGGCTT 540
TGTAATCCAATGGACATCACGCTATACTACTACCAGCAAACAGACGAAGCGAACAAATGG 600
ATCTCCATGGCTCTTCATGTACCATCAGAGTATGTCCACTTAACACTCAGACACTGGGA 660
ATAGGCTGTCTCACTACCGATGTTACGACCTTCGAAGAAATTGCGACTGCGGAGAAATTA 720
GCGATAACGGACGTCGTAGATGGCGTGAGTCACAAGCTTAACGTTACAACCGCGACTTGT 780
ACAATTCGTAACTGTAAGAAACTTGGTCCGCGAGAAAATGTAGCAGTTATACAAGTAGGT 840
GGCTCTGACATAATAGACATAACTGCAGATCCAACAACTGCACCACAAACCGAGAGAATG 900
ATGCGCATTAATTGGAAAAAATGGTGGCAAGTGTTCTACACCGTCGTTGATTATGTAAAT 960
CAGATAATCTCAACAATGTCCAAACGATCTAGATCACTGAACTCAGCAGCTTTTTATTAT 1020
AGAGTGTAGGTATAACTGAAGTTACAGCTGATGATGTGACC (SEQ ID NO: 4)
```

FIG. 15

Human Rotavirus
VP7

```
       ----,----+----,----+----,----+----,----+----,----+----,----+
    1  GGCTTTAAAAGAGAGAATTTCCGTCTGGCTAGCGGATAGCTCCTTTTAAT
   51  GTATGGTATTGAATATACCACAGTTCTATTTTATTTGATATCGTTCGTTC
  101  TTGTGAGTTATATTCTGAAAACCATAATAAAGATAATGGACTATATTATT
  151  TATAGAATAGCATTTGTAATTGTAGTATTATCAGTATTATCGAATGCACA
  201  AAATTATGGAATAAATTTGCCAATTACTGGATCTATGGATACAGCATATG
       ----,----+----,----+----,----+----,----+----,----+----,----+
  251  CTAACTCAACACAAGACAATAATTTTTTAGTTTCAACTTTATGTCTATAT
  301  TATCCATCAGAAGCTCCAACTCAAATTAGTGACACTGAATGGAAAGATAC
  351  ACTATCTCAGCTGTTTTTAACCAAAGGATGGCCGACAGGTTCAGTTTATT
  401  TTAATGAATATTCAAACGTTTTAGAATTTTCCATCGACCCAAAGCTATAC
  451  TGTGATTATAATGTTGTGCTAATTAGATTCGTTTCTGGTGAGGAGTTGGA
       ----,----+----,----+----,----+----,----+----,----+----,----+
  501  CATATCTGAATTAGCTGATCTAATACTGAATGAGTGGTTATGTAATCCAA
  551  TGGATATAACATTATATTATTACCAACAAACTGGAGAGGCAAACAAATGG
  601  ATATCAATGGGATCATCATGTACCGTTAAAGTGTGTCCATTAAATACTCA
  651  GACATTAGGAATTGGATGTCAAACGACAAATACAGCTACTTTTGAAACAG
  701  TTGCTGATAGCGAAAAATTGGCAATAATTGATGTTGTCTACATCGTAAAT
       ----,----+----,----+----,----+----,----+----,----+----,----+
  751  CATAAATTAAATATCACATCTACTACATGTACAATACGGAATTGTAATAA
  801  ACTAGGACCGAGAGAAAATGTGGCTATAATACAGGTTGGCGGTTCTAATA
  851  TATTAGATATAACAGCTGATCCCACAACTTCTCCACAAACAGAACGAATG
  901  ATGCGCGTAAACTGGAAAAAATGGTGGCAAGTATTCTACACTGTAGTTGA
  951  TTACATTAATCAGATAGTACAAGTAATGTCCAAAAGATCAAGATCGTTAG
       ----,----+----,----+----,----+----,----+----,----+----,----+
 1001  ATTCGTCAGCTTTCTATTATAGAGTGTAGATATATCCTAAAATAGAACTG
 1051  TTTGATGTGACC (SEQ ID NO: 6)
```

FIG. 16

SEQUENCE LISTING

<160> NUMBER OF SEQ ID NOS: 6

<210> SEQ ID NO 1
<211> LENGTH: 2359
<212> TYPE: DNA
<213> ORGANISM: Murine rotavirus VP4

<400> SEQUENCE: 1

| | | | | | |
|---|---|---|---|---|---|
| ggctataaaa | tggcttcact | catttataga | caactgctca | cgaattcctt | taccgtacat | 60 |
| atatctgatg | aaattgaaac | tattggagca | gagaagacac | aaaatgttac | agtgaatccc | 120 |
| ggtccattcg | cgcaaacggg | atacgcccca | gcaaactggg | ggccaggcga | aactaacgac | 180 |
| tcaacaacag | tagaaccaat | gcttgatgga | ccataccaac | caatagcgtt | cagtccgccg | 240 |
| ccagagtact | atatcatcct | ctccccgact | gcacccggag | taatcgctga | atgtacgaat | 300 |
| actgtcaacc | gctggatagc | aatcatagct | atagagccaa | acgtgtcaac | aacaaatcgt | 360 |
| acctacacat | tgttcggaat | tactgaacag | ctaacagtag | aaaacagctc | cgtggataaa | 420 |
| tggaagttta | tagacttcat | gaaaactcca | acaactggca | gctacgtccg | ttataacatt | 480 |
| ttgttgtcta | gcactaagct | atgcgcagtg | gcgaacgaca | cggacaattt | atactcctat | 540 |
| gttggagaaa | cgcctactgc | aggtcaggca | tactactctt | ctttcaatat | atttaaccta | 600 |
| accgcgcact | gtgacttcta | cattatacca | tggtcgcagc | aatcgttgtg | cacgcaatac | 660 |
| gttaataacg | gattaccgcc | gatccagaat | acaagaaatg | tagtgccaag | acatctgtca | 720 |
| gcgagatcaa | tcatcacaca | aagagcgcaa | cagaatgaag | acattgttgt | gtcaaagaca | 780 |
| tccttatgga | aagaaatgca | gtttaatagg | gacataacaa | tacgtttcaa | attcgcgaat | 840 |
| gcaataataa | agtctggcgg | cttgggatat | aattggtcag | agatctcttt | caaaccagcg | 900 |
| aactaccaat | acacgtacac | acgtgatggt | gaagaagtaa | ctgcgcatac | tacgtgctcg | 960 |
| gtaaacggtg | tgaacaactt | cgatttcttt | ggcggtacgc | tccctacgga | tttcggtatt | 1020 |
| tcgcggtacg | aagtgattaa | ggagaattca | ttcgtgtaca | tagactattg | ggacgactct | 1080 |
| caggctttca | gaaatatggt | ctatgtgcgc | tcactagcgg | ctgatttgaa | cactgtcgaa | 1140 |
| tgcactgggg | gggcgtacag | cttttcacta | ccagttgggc | aatggccggt | gatgacgggt | 1200 |
| ggtgcagtgt | ctttgcgagc | tgccggagtt | acactatcta | cacagttcac | agacttcgtg | 1260 |
| tcgctaaatt | cgttgagatt | taggtttcgt | ttgtcagtgg | aagaaccgtc | attcagtata | 1320 |
| acgagaacaa | gagtgtcagg | gctatacggc | ttgccagagc | gggatcctaa | caacggcaga | 1380 |
| gaatattacg | aaattgcagg | tagattttcg | ttaatatcat | tagtgccgtc | caacgataac | 1440 |
| tatcaaacac | cgataatgaa | ttcagttacg | gtgcggcaag | atctggagag | acagctaggc | 1500 |
| gaactacgac | gagaattcaa | cgcgctgtcg | caggaaatag | cgctgtcaca | gttggtggat | 1560 |
| ttagcgctac | tgccattaga | tatgttctca | atgttttcag | gcatcaaagc | aacgctcgac | 1620 |
| gtggcaaagt | caatggcaac | gaacgtgatg | aaaaaattca | aaaatcggg | actggccacg | 1680 |
| tcgatttcac | gcatgactga | gtcactatca | gatgcagctt | cctcagtgtc | tcggagtgag | 1740 |
| ctgcatacgc | tcagtcagtt | ccacgtcatc | agcttggaca | gacgtttcgt | agctgctgtg | 1800 |
| gccaacgtgg | aaaatgccgc | ctcaacagtt | tcaacacaga | cggccacaat | cagcagacgg | 1860 |
| ttgagactga | aggaaatcac | aacgcagact | gaaggcatga | acttcgatga | catctcagcc | 1920 |
| gctgtactta | aaactaagct | tgataaatca | gtacgaatcg | cgccgaacac | gctaccagac | 1980 |
| atagtaacag | aagcgtcaga | gaagttcatt | ccgaacagat | catacagagt | tataaacaac | 2040 |

-continued

```
aatgaagcat tcgaaactgg aactgacgga cgcttcttcg cataccgagt tgacactctt    2100
gaggaactgc cattcgacgt tcagaaattc gcatgccatg ctgcagagtc cccagtaatc    2160
tcagccatca ctgacttcaa gactttgaaa aatttgaacg ataactacgg aatctcgaaa    2220
gaacaggcct tcagtttatt acgctcagat ccgcgagtac tccgtgaatt tattaatcag    2280
gggaatccaa taatacgtaa tagaatagaa cagttaatta tgcagtgtag actgtgagca    2340
gtgtctagag gatgtgacc                                                 2359
```

```
<210> SEQ ID NO 2
<211> LENGTH: 1356
<212> TYPE: DNA
<213> ORGANISM: Human rotavirus VP6

<400> SEQUENCE: 2
```

```
ggcttttaaaa cgaagtcttc gacatggagg ttctgtattc attgtcaaaa actcttaaag     60
atgctaggga taagattgtt gaaggtacat tatattctaa tgttagtgat ctcattcagc    120
aatttaatca atgatagta accatgaatg gaaatgactt tcaaactgga ggaattggca    180
atttacctat tagaaattgg acatttgact ttggtctact aggtactacg ctgttaaacc    240
ttgatgctaa ttacgttgag actgcaagaa ctacaattaa gtattttatt gactttattg    300
ataatgtatg tatggatgaa atggcaagag agtctcaaag aaatggagta gctccacaat    360
ctgaggcatt gaggaagcta gccggtatta aatttaaaag aataaatttt aataattcat    420
cagaatatat agaaaattgg aatttacaaa atagaagaca gcgtaccgga tttgttttcc    480
ataaacctaa tatatttcca tactcagcat catttacttt aaataggtct caaccaatgc    540
atgacaattt aatgggaacc atgtggctta acgctggatc agaaattcaa gtggctggat    600
ttgactactc cgtgtgccta aatgctccag caaatattca gcagtttgaa catattgtcc    660
agcttaggcg tgcgctaact acagctacta taactttgct acctgatgca gaaagattta    720
gttttccaag agttattaat tcagcagatg gcgcaaccac atggttcttt aatccaatta    780
tcctaagacc aaacaatgta gaggtagaat ttttactgaa tggacaaatt attaatacat    840
atcaagctag atttggaact attatcgcaa gaaattttga tacaattcgt ctatcattcc    900
aattaatgcg tccaccaaac atgacgccag ccgtaaatgc attatttccg caagcacaac    960
cttttcaaca tcatgcaaca gttggactta cgttacgtat tgagtctgca gtttgtgaat   1020
cagtgcttgc ggatgcaaat gaaactttat tggcgaatgt tactgcagta cgtcaagagt   1080
atgctatagg cgttggacca gtatttccac caggcatgaa ttggactgag ctgattacta   1140
actattcacc atccagggaa gataaatttgc aacgtgtctt tacagtagcc tctatcagaa   1200
gcatgttaat taagtgagga ccagactaac catctggtat ccaatcttaa ttagcatgta   1260
gctatgtcaa gtcattcaga ctctacaagt aaggacatga tttcatgttc gctacgtaga   1320
gtaactgcat gaatgatcta gtgagaggat gtgacc                             1356
```

```
<210> SEQ ID NO 3
<211> LENGTH: 1356
<212> TYPE: DNA
<213> ORGANISM: Bovine rotavirus VP4

<400> SEQUENCE: 3
```

```
ggcttttaaa cgaagtcttc aacatggatg tcctgtactc cttgtcaaaa actcttaaag     60
atgctagaga caaaattgtc gaaggcacat tatactccaa tgtaagtgat ctaattcaac    120
```

-continued

```
aatttaatca aatgataatt actatgaatg gaaatgagtt ccaaactgga ggaattggta     180
atctaccgat tagaaattgg aattttgatt ttggattact cggaacaact ctactaaatt     240
tggatgccaa ctacgtcgaa acggcccgca atacaattga ttattttgta gattttgtag     300
ataatgtatg tatggatgaa atggttagag aatcacaaag aaatggaatt gcaccacaat     360
cagattcact tagaaagttg tcaggtatta aattcaaaag aataaatttt gacaattcat     420
cagaatacat agagaactgg aatttgcaaa acagaagaca aagaacgggt tttacatttc     480
ataaaccaaa cattttccct tactcagcgt cattcacact gaacagatca caaccagctc     540
atgataactt gatgggtacg atgtggctca atgcgggatc agaaattcag gtcgctggat     600
tcgattattc atgtgcaatc aatgcgccag ccaatacaca acaatttgag catattgtac     660
agctccgaag agtgttgact acagctacaa taactctttt accagatgca gaaagattta     720
gttttccaag agtgattaat tcagctgacg gagctactac atggtacttc aacccagtga     780
ttcttagacc aaataacgtt gaagtagagt ttctactaaa cgggcagata ataaatactt     840
accaagcaag atttggaacg atcatagcta gaaattttga tacaattaga ttgtcatttc     900
agttgatgag accaccaaat atgacaccag cggtagcggc gttatttcca aatgcgcagc     960
catttgaaca tcaggcaaca gtaggactca cgcttagaat tgaatctgca gtttgtgaat    1020
cagtgcttgc cgacgcaagt gaaacaatgc tagcaaatgt gacatctgtt agacaagaat    1080
acgcgatacc agttggacca gtttttccac caggtatgaa ttggactgat ttgatcacta    1140
actattcacc atctagagag gataatttgc agcgtgtatt tacagtggct tccattagaa    1200
gcatgcttgt caaatgagga ccaagctaac cacttggtat ccgactttgg tgagtatgta    1260
gctacgtcaa gctgtttgaa ctctgtaagt aaggatgcgt ctacgtattc gctacacaga    1320
gtaatcactc agatggcgta gtgagaggat gtgacc                              1356
```

<210> SEQ ID NO 4
<211> LENGTH: 1061
<212> TYPE: DNA
<213> ORGANISM: Murine rotavirus VP7

<400> SEQUENCE: 4

```
ggctttaaaa gagagaattt ccgtttggct agcggttagc tccttttaat gtatggtatt      60
gaatatacca cagctttaac tttcctgata tcatttcttt tattgcgcta catactaaaa     120
tcagtagtta aaattatgga ctttatagtt tacaggtttt tgtttgtaat tctaattttg     180
tcgccatgta ttaaagctca aaactacggc attaatcttc caattactgg ttcaatggac     240
actgcgtatg caaactcaac tcaaccggag acatttctga cttccactct atgcctttac     300
tatccaacag aagcagctac tgagataaag gataactcgt ggaaagacac gttatcgcaa     360
ctattcttaa cgaaaggatg gccaataggg tcagtctatt ttaaagaata caccgacata     420
gcagcgttct caatcgatcc acaactatac tgtgattaca acgtagtgct gatgaaatat     480
gacgcttcat tacaaatgga tatgtcggaa cttgcagact tgatactgaa tgaatggctt     540
tgtaatccaa tggacatcac gctatactac taccagcaaa cagacgaagc gaacaaatgg     600
atctccatgg gctcttcatg taccatcaga gtatgtccac ttaacactca gacactggga     660
ataggctgtc tcactaccga tgttacgacc ttcgaagaaa ttgcgactgc ggagaaatta     720
gcgataacgg acgtcgtaga tggcgtgagt cacaagctta acgttacaac cgcgacttgt     780
acaattcgta actgtaagaa acttggtccg cgagaaaatg tagcagttat acaagtaggt     840
ggctctgaca taatagacat aactgcagat ccaacaactg caccacaaac cgagagaatg     900
```

-continued

```
atgcgcatta attggaaaaa atggtggcaa gtgttctaca ccgtcgttga ttatgtaaat    960
cagataatct caacaatgtc caaacgatct agatcactga actcagcagc tttttattat   1020
agagtgtagg tataactgaa gttacagctg atgatgtgac c                       1061
```

<210> SEQ ID NO 5
<211> LENGTH: 2359
<212> TYPE: DNA
<213> ORGANISM: Human rotavirus VP4

<400> SEQUENCE: 5

```
ggctataaaa tggcttcgct catttataga cagcttctca ctaattcata ttcagtagat     60
ttacatgatg aaatagagca aattgggtca gaaaaaactc aaaacgtaac tgtaaatcca    120
ggtccatttg cccaaactag atatgctcca gtaaattggg gtcatggaga gataaatgat    180
tcaaccacag tagaaccaat tttagatggt cctatcagc ctactacatt taaaccactt    240
actgattatt ggatacttat taactcaaat acaaatggag tggtatacga gagtacgaat    300
aatagtgact tttggactgc agtagttgct attgaaccgc acgttatcca gtagataga    360 caatatactg tatttggtga aaataaacaa tttaatgtaa gaaatgattc agataaatgg    420 aagttttag aaatgtttag aggcagtagt caaaatgaat tttataatag acgtacacta    480
acttctgata ctaaactcgt aggaatatta aaatatggtg aaggatatg gacatttcat    540 ggtgaaacac cgagagctac tactgatagt tcaaatactg caaatttaaa cgatatatca    600
attataatac attcagaatt ttatattatc ccaaggtccc aagaatctaa gtgtaatgaa    660
tatattaaca atggtttgcc accaattcaa aatactagaa atgtagtacc attatcatta    720
tcatctagat ccatacagta taaagagca aagttatg aagatattac aatttcaaaa    780
acctcattat ggaaagaaat gcaatgtaat agggatatta taattagatt taaatttggt    840
aatagtattg taaaactggg gggactaggt tataaatggt ccgaaatatc atataaagca    900
gcaaattatc aatataatta tctacgtgat ggcgaacaag taactgcaca tactacttgc    960
tcagtaaatg gagtaaataa ttttagctac aacggaggat ctttacctac tgatttagt   1020 gtctcaaggt atgaagttat taaagaaaat tcttatgtat atgtagatta ttgggatgat   1080
tcaaaagcat ttagaaatat ggtatatgtc agatcattag cagctaattt gaactcagtg   1140
aaatgtacag gtggaagtta tgactttagt atacctgtag gtgcatggcc agtcatgaat   1200
ggtggcgctg tttcgttgca ttttgctgga gttacattat ctacgcaatt cacagatttc   1260
gtatcattga attcactacg atttagattt agtttgacag tggatgagcc atcttttta   1320 atattgagaa cacgtacggt gaatttgtac ggattaccag ctgcaaatcc aataatgga   1380 aatgaatact atgaaatatc aggaaggttt cgctcatttc tttagttcc aactaatgat   1440 gattatcaga ctccaattat gaattcagta acagtaagac aagatttaga acgtcaactt   1500 actgattac gagaggaatt taattcatta tcacaagaaa tagctatgtc acaattaatt   1560 gattagcgt tattaccttt agatatgttt tctatgtttt cggaattaaa aagtacaatt   1620
gatttgacta aatcaatggc aactagtgta atgaaaaaat ttagaaaatc aaaattagct   1680
acatcaattt cagaaatgac tcattcattg tcagacgcag catcatcagc atcaagaagc   1740
gtttctatca gatcgaatat atccacaatt tcgaattgga ctaatgtttc aaatgatgta   1800
tcaaatgtga ctaattcgtt gagtgatatt tcaacacaaa cgtctacaat cagtaagaac   1860
cttagattaa aagaaatgat tactcaaact gaaggaatga gttttgatga tatttcagcg   1920
```

```
gcagtattaa aaacaaaaat agatatgtct actcaaattg gaaagaatac tttacccgat      1980
atagtcacag aggcatctga gaaatttatt ccaaaacgat cgtatcgaat attgaaagat      2040
gatgaagtaa tggaaattaa tactgaaggg aaagtctttg catataaaat cgacacactt      2100
aatgaagtgc catttgatgt aaataaattt gctgaacttg taacaaattc tccagttata      2160
tcagcaataa tcgattttaa aacattaaaa aatttgaatg ataattatgg aattactcga      2220
atagaagcat taaatttaat taaatcgaat ccaaatgtat tacgtaattt cattaaccaa      2280
aataatccaa ttataaggaa tagaattgaa cagctaattc tacaatgtaa attgtgagaa      2340
cgctattgag gatgtgacc                                                   2359

<210> SEQ ID NO 6
<211> LENGTH: 1062
<212> TYPE: DNA
<213> ORGANISM: Murine rotavirus VP4

<400> SEQUENCE: 6
ggctttaaaa gagagaattt ccgtctggct agcggatagc tcctttttaat gtatggtatt       60 gaatatacca cagttctatt ttatttgata tcgttcgttc ttgtgagtta tattctgaaa      120
accataataa agataatgga ctatattatt tatagaatag catttgtaat tgtagtatta      180
tcagtattat cgaatgcaca aaattatgga ataaatttgc caattactgg atctatggat      240
acagcatatg ctaactcaac acaagacaat aattttttag tttcaacttt atgtctatat      300
tatccatcag aagctccaac tcaaattagt gacactgaat ggaaagatac actatctcag      360 ctgttttaa ccaaaggatg gccgacaggt tcagtttatt ttaatgaata ttcaaacgtt      420
ttagaatttt ccatcgaccc aaagctatac tgtgattata atgttgtgct aattagattc      480
gtttctggtg aggagttgga catatctgaa ttagctgatc taatactgaa tgagtggtta      540
tgtaatccaa tggatataac attatattat taccaacaaa ctggagaggc aaacaaatgg      600
atatcaatgg gatcatcatg taccgttaaa gtgtgtccat taaatactca gacattagga      660
attggatgtc aaacgacaaa tacagctact tttgaaacag ttgctgatag cgaaaaattg      720
gcaataattg atgttgtcta catcgtaaat cataaattaa atatcacatc tactacatgt      780
acaatacgga attgtaataa actaggaccg agagaaaatg tggctataat acaggttggc      840
ggttctaata tattagatat aacagctgat cccacaactt ctccacaaac agaacgaatg      900
atgcgcgtaa actggaaaaa atggtggcaa gtattctaca ctgtagttga ttacattaat      960
cagatagtac aagtaatgtc caaaagatca agatcgttag attcgtcagc tttctattat     1020
agagtgtaga tatatcctaa aatagaactg tttgatgtga cc                        1062
```

DNA VACCINES AGAINST ROTAVIRUS INFECTIONS

CROSS-REFERENCE TO RELATED APPLICATION

This is a continuation of U.S. appclation Ser. No. 08/842,563, filed Apr. 15, 1997, (abandoned) which is a continuation of U.S. application Ser. No. 08/426,169, filed Apr. 20, 1995, now U.S. Pat. No. 5,620,896, which is a Continuation-in-Part of earlier filed (pending) U.S. application Ser. No. 08/187,879, filed Jan. 27, 1994, which is a Continuation-in-Part of U.S. application Ser. No. 08/009,833, filed Jan. 27, 1993, now U.S. Pat. No. 5,643,578 which is a Continuation-in-Part of application Ser. No. 07/855,562, filed Mar. 23, 1992, now abandoned, which applications are incorporated herein by reference in their entirety.

BACKGROUND OF THE INVENTION

Rotavirus infections are ubiquitous throughout mammalian and avian species. The viruses appear to be species-specific although cross-species infections can be produced experimentally and may occur in nature to a limited extent. Infection occurs after ingestion of viral particles and is restricted to the mature absorptive epithelial cells on the villi of the small intestine. Multiplication of rotaviruses within these cells results in lysis, and eventual loss of normal villous structure. Copious acute watery diarrhea occurs as a result of intestinal damage and replacement of absorptive cells by secreting cells from the villous crypts.

Viral gastroenteritis resulting from rotavirus infection is a common cause of epidemic diarrhea in infants from 6 to 24 months of age. Untreated rotavirus diarrhea in young children can be rapidly fatal. The recovery phase in some young children can be very protracted (involving villous atrophy associated with lactose intolerance) and can lead to or exacerbate existing malnutrition (Bishop, R. F. (1993) Vaccine 11:247–254). In fact, rotaviruses appear to be responsible for at least one half of the cases of infantile diarrhea that require hospitalization, and have been estimated to cause 500,000 to 1,000,000 human deaths worldwide each year.

Rotavirus has occasionally been reported as a cause of disease in miliary populations, in hospital workers, and as a cause of travelers' diarrhea. The most common setting for adult disease is that associated with parenting infected infants. Approximately 50% of parents experience rotavirus infection at the time of infant rotavirus disease; one-third of these adult infections are symptomatic (Offit, P. A. and Clark, H. F. (1995) In: *Principles and Practices of Infectious Diseases*, 4th ed., Mandell, G. L. et al., pp. 1448–1455) and references cited therein). Moreover, rotaviruses are known to cause diarrhea in agriculturally valuable animals such piglets, lambs, and foals, as well as in other animals such as rabbits, deer, and monkeys.

Currently, viral gastroenteritis therapy is limited to supportive measures, since there are no effective antiviral agents available for specific treatment. Prevention of rotavirus illness would be a major contribution to reduction of morbidity from gastroenteritis (Joklik, W. K., ed., *Virology*, 2nd. ed. (1985), Appleton-Century-Crofts, Norwalk, Conn., pp. 236–238).

Vaccination with inactivated or attenuated organisms or their products has been shown to be an effective method for increasing host resistance and ultimately has led to the eradication of certain common and serious infectious diseases. The use of vaccines is based on the stimulation of specific immune responses within a host.

Rotavirus vaccine development began with tests in children using live, attenuated vaccines from animal rotavirus strains. Two candidate vaccines, RIT4237 and WC3, both bovine serotype 6 viruses, have progressed to field trials (Estes, M. K. and Cohen, J. (1989), Microbiol. Rev. 53:410–449). The bovine strain RIT 4237 showed good efficacy when tested initially in developed countries, but failed to provide protection when tested in developing countries, and has been removed from further testing (Estes, M. K. and Cohen, J. (1989), supra).

Effective vaccines have been developed for relatively few of the infectious agents that cause disease in domestic animals and man. This reflects technical problems associated with the growth and attenuation of virulent strains of pathogens.

Other approaches to the development of candidate vaccines include "reassortants," which contain a single gene encoding the outer capsid glycoprotein from human virus serotypes on a rhesus rotavirus background. Such reassortant vaccines have been produced as potential vaccines to induce homotypic immune response to the four human serotypes (Midthun et al., J. Virol. (1985) 53:949–954; and Estes M. K. and Cohen, J. (1989), supra).

Group A rotaviruses contain seven structural proteins. Of these, the two outer capsid proteins, VP4 and VP7, appear to be the major proteins that induce humoral and cellular immune responses (Estes, M. R. and Cohen, J. (1989) supra; and Dharakul, R. et al. (1991) J. Virol. 65:5928–5932).

VP7 has been the subject of experimental vaccine studies because it is the most abundant outer capsid protein, accounting for approximately 30% of the total virion protein, compared to 1.5% for VP4 (Estes M. R. and Cohen, J. (1989), supra). However, inoculation with vaccinia or adenovirus recombinant virus containing a gene encoding a recombinant $VP7_{SC}$ gene, or a wild type SA-11 VP7 gene did not elicit protection against homologous rotavirus challenge in an adult mouse model (Dormitzer, P. et al. (1993) Abstr. IXth Intl. Congress of Virology, W21-2, p. 43; and Audio Tape, Dormitzer, P. et al. (Aug. 10, 1993) IXth Intl. Congress of Virology, Workshop W21).).

The major component of the inner capsid, VP6, is antigenically conserved among different serotypes of group A rotaviruses infecting animals, birds, and humans (Bellamy A. R. and Both, G. W., Adv. Virus Res. (1990) 38:1–43; Estes, M. (1991) In: *Fundamental virology*, 2nd edn, Fields B. N. and Knipe, D. M., eds., pp. 619–642). VP6 is highly immunogenic and antigenic (Estes, M. R. and Cohen, J. (1989), supra) but, paradoxically, does not generate neutralizing antibodies when assayed in vitro. VP6 coding sequence cloned into a vaccinia virus vector and administered to adult mice did not protect against rotavirus infection (Dormitzer, P. et al. (1993) Abstr. IXth Intl. Congress of Virology, W21-2, p. 43; and Audio Tape, Dormitzer, P. et al. (Aug. 10, 1993) IXth Intl. Congress of Virology, Workshop W21). Further, monoclonal antibodies to VP6 do not protect infant mice against rotavirus diarrhea (Riepenhoff-Talty, M. et al. (1987) Adv. Exp. Med. Biol. 216B:1015–1023).

SUMMARY OF THE INVENTION

The invention relates to specific DNA vaccines and methods of providing protective immunity to vertebrates, particularly humans and pigs, against a rotavirus infection. "Protective immunity" conferred by the method of the invention can elicit humoral and/or cell-mediated immune responses to rotavirus infection, but more importantly interferes with the activity, spread, or growth of a rotavirus following a subsequent challenge after vaccination. The DNA vaccines of the invention are transcription units containing DNA encoding a rotavirus polypeptide or protein. In the method of the present invention, a DNA vaccine is administered to an individual in whom protective immunization is desired.

An object of the invention is to provide an immune response and protective immunity to an animal using a DNA vaccine encoding a rotavirus protein as it has the potential of achieving high levels of protection in the virtual absence of side effects. Such DNA vaccines are also stable, easy to administer, and sufficiently cost-effective for widespread distribution.

An object of the invention is provide protective immunity to an inoculated host. If the inoculated host is a female animal, an object of the invention is to provide protection in the offspring of that female.

The invention features a DNA vaccine containing a rotavirus DNA transcription unit (i.e., an isolated nucleotide sequence encoding a rotavirus protein or polypeptide). The nucleotide sequence is operably linked to transcriptional and translational regulatory sequences for expression of the rotavirus polypeptide in a cell of a vertebrate. Preferably the rotavirus polypeptide encoded by the DNA vaccine of the invention is VP4, VP6, and/or VP7. Preferably, the nucleotide sequence encoding the rotavirus polypeptide is contained in a plasmid vector.

The DNA vaccines can be administered to mammals such as pigs or humans susceptible to rotavirus infection and rotavirus-caused disease.

The DNA vaccines of the invention are preferably contained in a physiologically acceptable carrier for in vivo administration to a cell of a vertebrate. Administration of the DNA vaccines of the invention provide an immune response or protective immunity in the vertebrate to disease caused by rotavirus infection. Protective immunity is homologous, homotypic, heterotypic, or heterotypic.

As used herein, the term "homotypic," referring to viral protection or viral challenge, means that the inoculating antigen and the challenge antigen are derived from the same viral serotype.

As used herein, the term "heterotypic," referring to viral protection or viral challenge, means that the inoculating antigen and the challenge antigen are derived from different viral serotypes.

As used herein, the term "homologous," referring to viral protection or viral challenge, means that the inoculating antigen and the challenge antigen are derived from rotaviruses having the same species specificity.

As used herein, the term "heterologous," referring to viral protection or viral challenge, means that the inoculating antigen and the challenge antigen are derived from rotaviruses having different species specificity.

The invention also features a method of providing an immune response and protective immunity to a vertebrate against an infectious rotavirus. The method includes administering to a cell of a vertebrate a DNA transcription unit encoding a desired rotavirus antigen operably linked to a promoter sequence. Expression of the DNA transcription unit in the cell elicits a humoral immune response, a cell-mediated immune response, or both against the infectious rotavirus.

The promoter operably linked to the DNA transcription unit is of nonretroviral or retroviral origin. Preferably the promoter is the cytomegalovirus immediate-early enhancer promoter. The desired rotavirus antigen encoded by the DNA transcription unit is VP4, VP6, and/or VP7.

Protective immunity provided by administration of the DNA transcription unit of the invention is homologous, homotypic, heterotypic, or heterologous. The infectious rotavirus can be of the same strain or the same serotype as the rotavirus from which the DNA encoding a desired antigen is obtained. Alternatively, the infectious rotavirus can be of a different strain, a different serotype, or different species specificity as the rotavirus from which the DNA encoding a desired antigen is obtained.

The method of providing an immune response and protective immunity is practiced on a vertebrate, preferably a mammal such as a pig or other animal. The vertebrate can also be a human susceptible to infection by rotavirus and susceptible to disease caused by rotavirus. The human may be an infant less than 3 years of age, human caring for an infected infant, or an immunocompromised human of any age.

The DNA transcription unit of the method of the invention is preferably contained in a physiologically acceptable carrier and is administered to the vertebrate by routes including, but not limited to, inhalation, intravenous, intramuscular, intraperitoneal, intradermal, and subcutaneous administration. The DNA transcription unit in a physiologically acceptable carrier can also be administered by being contacted with a mucosal surface of the vertebrate.

Preferably, administration is performed by particle bombardment using gold beads coated with the DNA transcription units of the invention. Preferably, the gold beads are 1 $\mu$m to 2 $\mu$m in diameter. The coated beads are preferably administered intradermally, intramuscularly, by organ transfection, or by other routes useful in particle bombardment and known to those of ordinary skill in the art.

The term "immune response" refers herein to a cytotoxic T cells response or increased serum levels of antibodies to an antigen, or to the presence of neutralizing antibodies to an antigen, such as a rotavirus protein. The term "protection" or "protective immunity" refers herein to the ability of the serum antibodies and cytotoxic T cell response induced during immunization to protect (partially or totally) against disease caused by an infectious agent, such as a rotavirus. That is, a vertebrate immunized by the DNA vaccines of the invention will experience limited growth and spread of an infectious rotavirus.

The term "promoter sequence" herein refers to a minimal sequence sufficient to direct transcription. Also included in the invention is an enhancer sequence which may or may not be contiguous with the promoter sequence. Enhancer sequences influence promoter-dependent gene expression and may be located in the 5' or 3' regions of the native gene. Expression is constitutive or inducible by external signals or agents. optionally, expression is cell-type specific, tissue-specific, or species specific.

By the term "transcriptional and translational regulatory sequences" is meant nucleotide sequences positioned adjacent to a DNA coding sequence which direct transcription or translation of a coding sequence (i.e. facilitate the production of, e.g., VP4, VP6, or VP7 protein). The regulatory nucleotide sequences include any sequences which promote sufficient expression of a desired coding sequence (such as VP4, VP6, or VP7) and presentation of the protein product to the inoculated animal's immune system such that protective immunity is provided.

By the term "operably linked to transcriptional and translational regulatory sequences" is meant that a polypeptide coding sequence and minimal transcriptional and translational controlling sequences are connected in such a way as to permit polypeptide expression when the appropriate molecules (e.g., transcriptional activator proteins) are bound to the regulatory sequence(s). In the present invention, polypeptide expression in a target vertebrate cell is particularly preferred.

The term "isolated DNA" means DNA that is free of the genes and other nucleotide sequences that flank the gene in the naturally-occurring genome of the organism from which the isolated DNA of the invention is derived. The term therefore includes, for example, a recombinant DNA which is incorporated into a vector; into an autonomously replicating plasmid or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequences.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

BRIEF DESCRIPTION OF THE DRAWINGS

FIG. 11 is a nucleotide sequence (SEQ ID NO:1) encoding a murine strain EW rotavirus VP4 protein.

FIG. 12 is a nucleotide sequence (SEQ ID NO:5) encoding a human rotavirus VP4 protein.

FIG. 13 is a nucleotide sequence (SEQ ID NO:2) encoding a human rotavirus VP6 protein.

FIG. 14 is a nucleotide sequence (SEQ ID NO:3) encoding a bovine rotavirus VP6 protein.

FIG. 15 is a nucleotide sequence (SEQ ID NO:4) encoding a murine strain EW VP7 protein.

FIG. 16 is a nucleotide sequence (SEQ ID NO:6) encoding a human rotavirus VP7 protein.

DETAILED DESCRIPTION

Figure 1A:
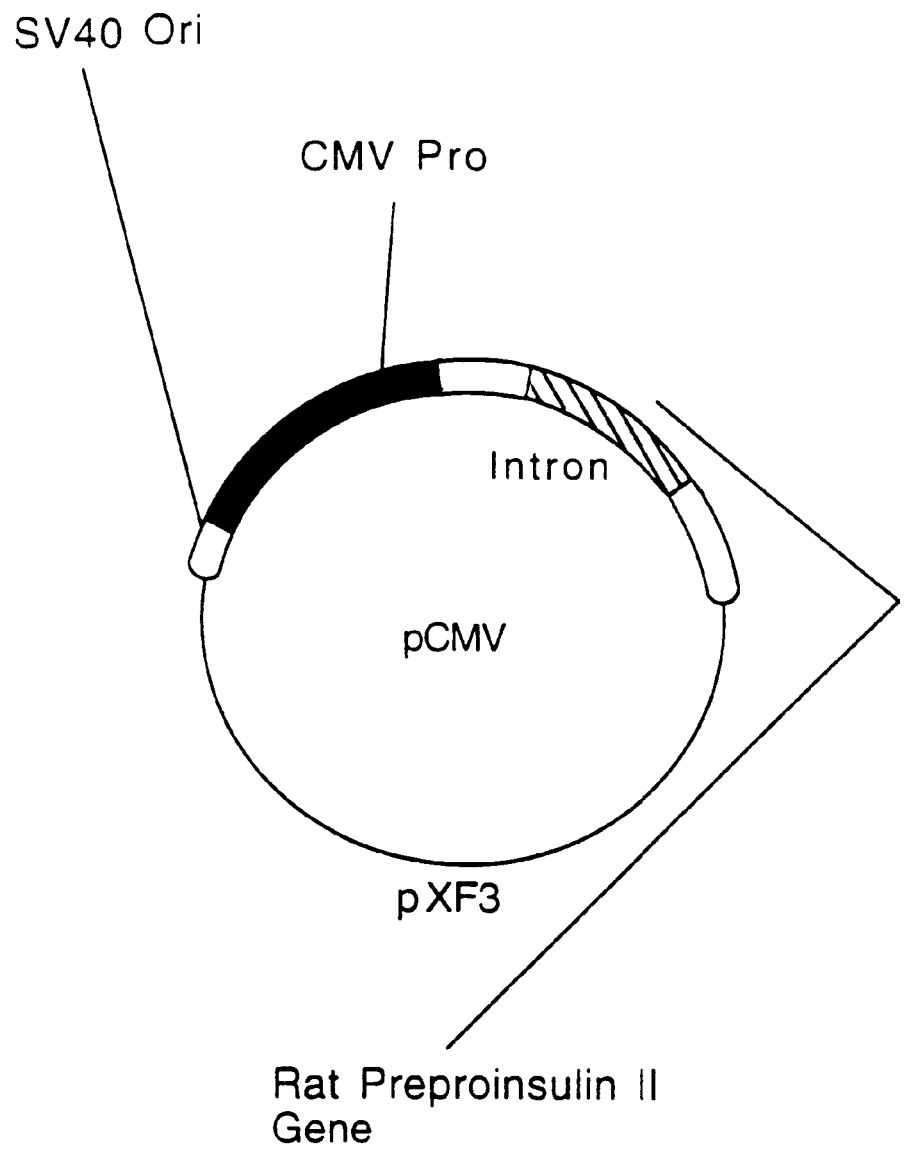
FIG. 1A is a schematic representation of control plasmid pCMV, a bacterial plasmid comprising a replication competent retroviral vector. The plasmid includes the CMV (cytomegalovirus) promoter/enhancer element and the rat preproinsulin gene.

This invention relates to a method of providing protective immunity to vertebrates, including humans, against rotavirus infection or disease caused by a rotavirus infection. Protective immunity of the invention elicits humoral and/or cell-mediated immune responses which interfere with the infectivity or activity of the rotavirus, or which limit its spread or growth, resulting in protection against subsequent challenge by the rotavirus. According to the present invention, a DNA transcription unit is administered to an individual in whom immunization and protection is desired.

DNA Transcription Units

A DNA transcription unit is a polynucleotide sequence, bounded by an initiation site and a termination site, that is transcribed to produce a primary transcript. As used herein, a "DNA transcription unit" includes at least two components: (1) antigen-encoding DNA, and (2) a transcriptional promoter element or elements operatively linked for expression of the antigen-encoding DNA. Antigen-encoding DNA can encode one or multiple antigens, such as antigens from two or more different rotavirus proteins. The DNA transcription unit can additionally be inserted into a vector which includes sequences for expression of the DNA transcription unit.

A DNA transcription unit can optionally include additional sequences such as enhancer elements, splicing signals, termination and polyadenylation signals, viral replicons, and bacterial plasmid sequences. In the present method, a DNA transcription unit (i.e., one type of transcription unit) can be administered individually or in combination with one or more other types of DNA transcription units.

DNA transcription units can be produced by a number of known methods. For example, DNA encoding the desired antigen can be inserted into an expression vector (see, for example, Sambrook et al., *Molecular Cloning, A Laboratory Manual*, 2d, Cold Spring Harbor Laboratory Press (1989)). With the availability of automated nucleic acid synthesis equipment, DNA can be synthesized directly when the nucleotide sequence is known, or by a combination of polymerase chain reaction (PCR), cloning, and fermentation. Moreover, when the sequence of the desired polypeptide is known, a suitable coding sequence for the polynucleotide can be inferred.

The DNA transcription unit can be administered to an individual, or inoculated, in the presence of adjuvants or other substances that have the capability of promoting DNA uptake or recruiting immune system cells to the site of the inoculation. It should be understood that the DNA transcription unit itself is expressed in the host cell by transcription factors provided by the host cell, or provided by a DNA transcription unit.

The "desired antigen" can be any antigen or combination of antigens from a rotavirus. The antigen or antigens can be naturally occurring, or can be mutated or specially modified. The antigen or antigens can represent different forms, such as subgroups (clades), subtypes, or serotypes of rotavirus. These antigens may or may not be structural components of a rotavirus. The encoded antigens can be translation products or polypeptides. The polypeptides can be of various lengths, and can undergo normal host cell modifications such as glycosylation, myristoylation, or phosphorylation. In addition, they can be designated to undergo intracellular, extracellular, or cell-surface expression. Furthermore, they can be designed to undergo assembly and release from cells.

Potential pathogens for which the DNA transcription unit can be used include DNA encoding antigens derived from any serotype or strain of rotavirus. It is to be understood that this list does not include all potential pathogens against which a protective immune response can be generated according to the methods herein described.

Administration of DNA Transcription Units

An individual can be inoculated through any parenteral route. For example, an individual can be inoculated by intravenous, intraperitoneal, intradermal, subcutaneous, inhalation, or intramuscular routes, or by particle bombardment using a gene gun. Muscle is a useful site for the delivery and expression of DNA transcription unit-encoded polynucleotides, because animals have a proportionately large muscle mass which is conveniently accessed by direct injection through the skin. A comparatively large dose of polynucleotides can be deposited into muscle by multiple and/or repetitive injections, for example, to extend therapy over long periods of time. Muscle cells are injected with polynucleotides encoding immunogenic polypeptides, and these polypeptides are presented by muscle cells in the context of antigens of the major histocompatibility complex to provoke a selected immune response against the immunogen (see, e.g., Felgner, et al. W90/11092, herein incorporated by reference).

The epidermis is another useful site for the delivery and expression of polynucleotides, because it is conveniently accessed by direct injection or particle bombardment. A comparatively large dose of polynucleotides can be deposited in the epidermis by multiple injections or bombardments to extend therapy over long periods of time. In immunization strategies of the invention, skin cells are injected with polynucleotides coding for immunogenic polypeptides, and these polypeptides are presented by skin cells in the context of antigens of the major histocompatibility complex to provoke a selected immune response against the immunogen.

In addition, an individual can be inoculated by a mucosal route. The DNA transcription unit can be administered to a mucosal surface by a variety of methods including DNA-containing nose-drops, inhalants, suppositories, microsphere encapsulated DNA, or by bombardment with DNA coated gold particles. For example, the DNA transcription unit can be administered to a respiratory mucosal surface, such as the nares or the trachea.

Any appropriate physiologically compatible medium, such as saline for injection, or gold particles for particle bombardment, is suitable for introducing the DNA transcription unit into an individual.

Immunization as described herein was accomplished with various DNA transcription units encoded on plasmid vectors that express different rotavirus proteins. The DNA transcription units described herein are representative of the types of transcription units that can be used in the current invention. The DNA transcription units can encode antigens from a single rotavirus species, including antigens from different subgroups (clades) or subtypes of the specie, and can additionally encode antigens from more than one rotavirus species.

Rotavirus DNA Transcription Units

In one embodiment of the current invention, immunization was accomplished using a DNA transcription unit encoding either of two murine rotavirus neutralizing capsid proteins, VP4 (SEQ ID NO:1; FIG. 11) or VP7 (SEQ ID NO:4; FIG. 15), or the internal core protein, VP6. DNA expression plasmids for the VP4, VP6, and VP7 protein were used to provide protection against challenge with an infectious rotavirus. An adult mouse model first described in Ward et al., *J. Virol.*, 64:5070–5075 (1990) (incorporated herein by reference) was used to test for protection.

The adult mouse model is convenient in assessing protection against an infectious agent by increasing the time period within which to perform the study. In this model, adult BALB/c mice (6 weeks or older) inoculated with a rotavirus do not show disease symptoms but, instead, exhibit infection as viral shedding in the feces for approximately one week post-infection. Virus shedding in feces is conveniently measured and quantitated by ELISA. Studies involving quantitation of viral shedding in adult mice is preferred over studies in which disease symptoms are observed in infant mice because the latter studies are hindered by the short period in which infant mice are susceptible to rotavirus illness (from birth to 15 days of age).

In the systemic strategies presented herein, an effective DNA dosage will generally be in the range of about 1 μg/kg to about 50 μg/kg, preferably about 10–25 μg/kg of body weight of the animal. However, as will be appreciated, this dosage will vary in a manner apparent to those of ordinary skill in the art according to the particular DNA used, the particular polypeptide encoded by the DNA, and the vertebrate being inoculated. For delivery of VP4, VP6, or VP7 to a vertebrate, such as a mouse, for example, adequate levels of translation are achieved with a DNA dosage of about 20 μg/kg of mouse body weight (see Example 3). From this information, dosages for other immunogenic polypeptides and other vertebrates, such as a pig or human, can be readily determined.

The following Examples describe vaccination trials using direct DNA inoculations designed for use in rotavirus immunoprotection. Vaccination trials for rotavirus were conducted using an adult mouse model. The adult mouse model demonstrated antibody and cytotoxic T-cell activity in animals inoculated with DNA transcriptional units for rotavirus protein, wherein animals inoculated with control DNA exhibited no antibody or cytotoxic T-cell activity for rotavirus. Protective immunity was also observed when the adult mice immunized with the DNA vaccine of the invention were subsequently challenged with rotavirus.

The current invention is illustrated by the following examples, which are not to be construed as limiting in any way.

EXAMPLES

Example 1
DNA Constructs for Immunization of Mice Using a DNA Transcription Unit Encoding a Rotavirus Protein A plasmid construct referred to as pCMV/VP7 places cDNA for murine rotavirus capsid protein, VP7 (SEQ ID NO:4), under the transcriptional control of the human CMV (cytomegalovirus) immediate-early enhancer/promoter element and the rat preproinsulin II gene. The pCMV plasmid without a rotaviral insert is a derivative of the pBC12/CMV plasmid of Dr. Bryan Cullen, Duke University, Durham, N.C. as described in Cullen, B. R., *Cell* 45:973–982 (1986).

The pCMV/VP7 plasmid expresses VP7, a murine rotavirus neutralization capsid protein. VP7 cDNA (SEQ ID NO:4) from EDIN EW strain murine rotavirus was obtained from Dr. Harry Greenberg, Stanford University, Stanford, Calif., USA (Dunn, S. J. et al. (1994) Virology 203:250–269; and can be obtained using standard techniques based on the complete sequence disclosed herein (SEQ ID NO:4) and in GenBank accession number U08430). For the purpose of the experiments described herein, murine VP7 cDNA (SEQ ID NO:4) was inserted between the BamHI and HindIII sites of the pCMV/control vector in an orientation for expression of the VP7 coding sequence. Another source of VP7 coding sequence is from porcine rotavirus VP7 (Gorziglia, M. et al. (1988) Nucl. Acids Res. 16:775).

Example 2
Immunizations by Intradermal Particle Bombardment Delivery of DNA to Mice Intradermal administration of DNA by particle bombardment was used to deliver DNA for expression of a rotavirus gene in skin cells. The Accell particle bombardment device ("gene gun"; Agracetus, Middleton, Wis.) was employed to deliver DNA-coated gold beads to the epidermis of mice.

Plasmid DNA was affixed to gold particles by adding 10 mg of 0.95 μm gold powder (Degussa, South Plainfield, N.J.), and an appropriate amount of plasmid DNA, to a 1.5-ml centrifuge tube containing 50 μl of 0.1 M spermidine. Plasmid DNA and gold were co-precipitated by the addition of 50 μl of 2.5 M CaCl$_2$ during vortex mixing, after which the precipitate was allowed to settle and was washed with absolute ethanol and resuspended in 2.0 ml of ethanol. The gold/DNA suspension was transferred to a capped vial and immersed in a sonicating water bath for 2–5 seconds to resolve clumps. The 163 μl of the gold/DNA suspension was layered onto 1.8 cm×1.8 cm Mylar sheets and allowed to settle for several minutes after which the meniscus was broken and excess ethanol was removed by aspiration. Gold/DNA-coated mylar sheets were dried and stored under vacuum. The total amount of DNA per sheet was a function of the DNA/gold ratio and ranged from 0.2 to 0.0002 μg per sheet.

Animals were anesthetized with 30 μl of Ketaset/Rompun (10:2). Abdominal target areas were shaved and treated with Nair (Carter-Wallace, New York) for two minutes to remove residual stubble and stratum corneum. Target areas were thoroughly rinsed with water prior to gene delivery. DNA-coated gold particles were delivered into abdominal skin with the Accell instrument, which employs an electric spark discharge as the motive force. Each animal received two nonoverlapping deliveries per immunization, at a discharge voltage of 17 kV. Particle bombardment technology is presented in the following articles, herein incorporated by reference: Yang, M. S. et al., (1990) Proc. Natl. Acad. Sci. USA 87:9568–9572; Yang N.-S. (1992) CRC Crit. Rev. Biotechnol. 12:335–356; and cheng, L. et al. (1993) Proc. Natl. Acad. Sci. USA 90:4455–4459.

The beads deliver DNA into cells, where the DNA dissolves and can be expressed (Yang, M. S. et al. (1991) Proc. Natl. Acad. Sci. USA 88: 2726–2730). Expression is transient, with most of the expression being lost within 2–3 days due to the normal sloughing of the epidermis (Williams, R. S. et al., Proc. Natl. Acad. Sci. USA 88: 2726–2730 (1991)).

These particle bombardment techniques can be easily adapted for use in human patients using human rotavirus DNA vaccines as described below.

Example 3
Inducing an Immune Response in Mice Using the pCMV/VP7 Plasmid

Figure 1B:
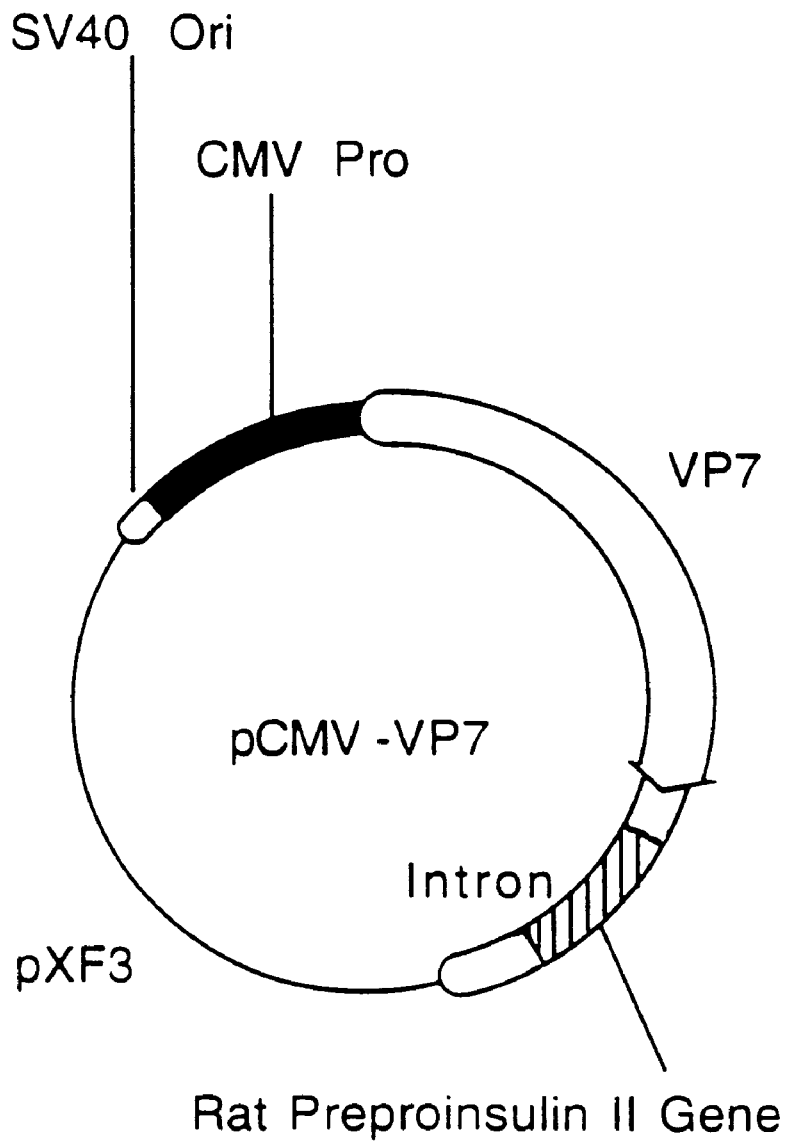
FIG. 1B is a schematic representation of a plasmid referred to as the "pCMV/VP7 plasmid," which comprises a pCMV control plasmid and a rotavirus antigen DNA transcription unit encoding VP7 protein.

A rotavirus DNA transcription unit was tested for its ability to induce an immune response in mice. The pCMV/VP7 plasmid and the control plasmid used in this experiment to vaccinate mice against rotavirus are depicted in FIGS. 1A and 1B.

The DNA vaccine pCMV/VP7 construct was inoculated into BALB/c (H-2$^d$) mice by gene gun delivery of DNA-coated gold beads into the epidermis as described above. The dose given was 0.4 μg of DNA per mouse. This dose was previously determined to be optimal for DNA vaccination against influenza virus in mice (Fynan, E. F. et al. (1993) PNAS USA 90:11478–11482). Two inoculations were given at 4-week intervals. The boosts used the same DNA dose and sites of inoculation as the vaccinations. Mice were tested for serum antibody levels and CTL responses 2 to 4 weeks after the second inoculation.

Serum antibody levels were determined by ELISA against EDIM rotavirus (Epizootic Diarrhea In Mice) for mice receiving EDIM strain EW virus VP7 DNA (as pCMV/VP7) or control DNA (as pCMV). Six mice were tested per group. The neutralization assay was performed as described in Dunn, S. J. et al. (1994), supra. The EDIM strain EW virus was obtained from H. B. Greenberg, Stanford University, Stanford, Calif., USA. Age-matched mice were inoculated with pCMV/VP7 DNA or pCMV/control DNA using the gene gun as described above or were administered live EDIM virus by oral gavage at a dosage of 100 ID$_{50}$/mouse.

The relative antibody production in adult mice following inoculation of the DNA vaccine and a live virus are compared in Table 1.

TABLE 1

Serum Anti-VP7 Antibody Titers Following Inoculation
[Mean Antibody Titer][1]

| Inoculum | Preinoculation | | 4 weeks Postinoculation | |
|---|---|---|---|---|
| | ELISA | Neutralization | ELISA | Neutralization |
| pCMV/VP7 | <50 | <50 | 400 | 100 |
| pCMV/control | <50 | <50 | <50 | <50 |
| EDIM virus | <50 | <50 | 800 | 200 |

The results in Table 1 show that serum antibody to EDIM virus developed only in mice receiving the plasmid containing the wild-type VP7 coding sequence (SEQ ID NO:4) or live EDIM virus. The titers obtained in sera taken at one month after the second DNA inoculation were 1:200 in mice receiving pCMV/VP7 and 1:800 in mice inoculated with EDIM virus. Antibody titers remained below 1:50 in mice inoculated with the control DNA.

Figure 2:
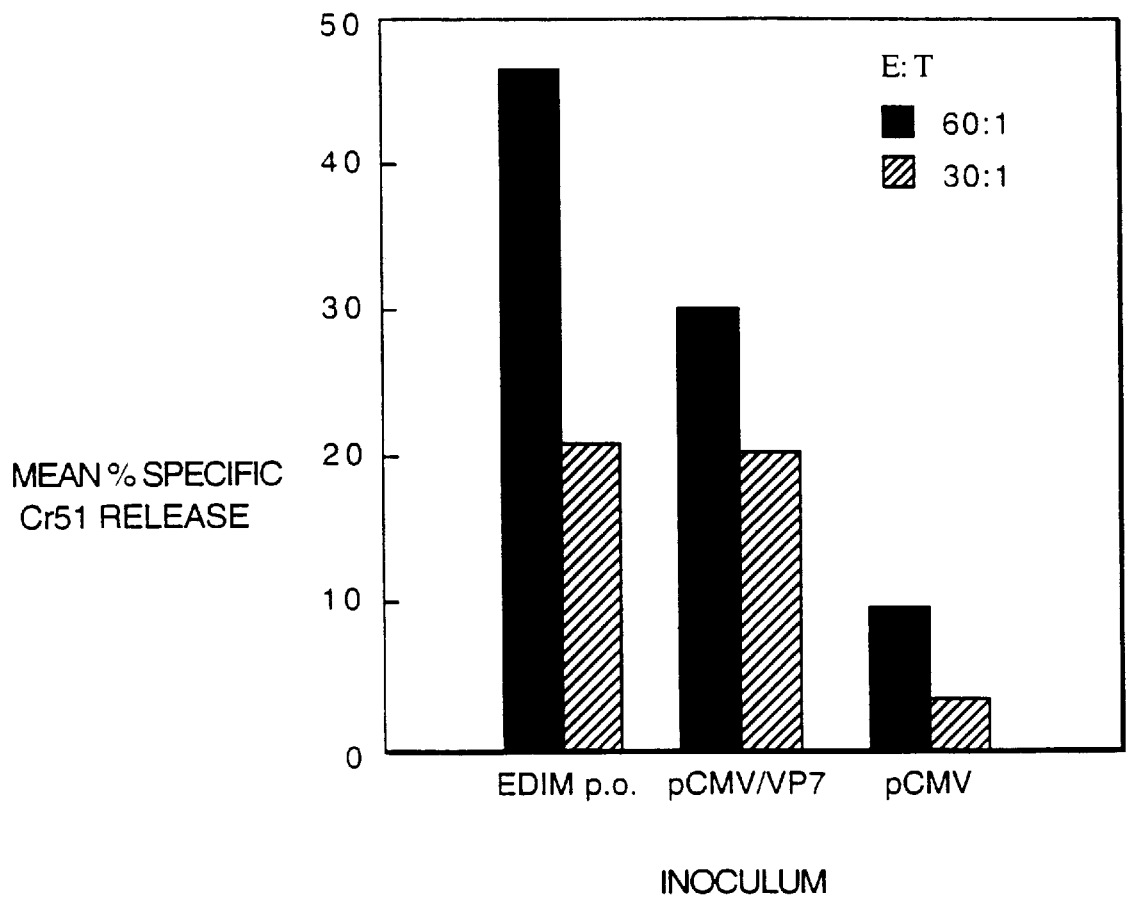
FIG. 2 is a bar graph depicting the cytotoxic T cell response of mice inoculated by gene gun with EDIM (Epizootic Diarrhea In Mice) VP7 rotavirus cDNA in comparison with controls. Solid bars represent an effector cell to target cell ratio of 60:1, and striped bars represent an effector cell to target cell ratio of 30:1.

It was also found that plasmid pCMV/VP7 was able to induce a cytotoxic T cell (CTL) response against murine rotavirus-infected cells. Cellular immune response was determined by measuring CTL activity in adult mice which were vaccinated with pCMV/VP7 or were given EDIM virus, as was done for the induction of serum antibodies in Example 2. Memory CTL activity was measured after in vitro stimulation. Splenic lymphocytes from DNA-treated or EDIM-infected mice were stimulated in vivo with EDIM virus. The activity of these effector lymphocytes was measured by a standard chromium-release CTL assay. EDIM-infected P815 ($H-2^d$) cells were used as target cells (P815 ($H-2^d$) cells may be obtained from ATCC as TIB 64). Separate experiments were performed in which effector cell to target cell (E:T) ratios were 60:1 (filled bars) or 30:1 (striped bars) as shown in FIG. 2. The results using the two different E:T ratios indicate that increasing the number of total cells increases the number of effector cells contacted with the target cells in the CTL chromium-release assay. Thus, the 60:1 E:T experiment shows increased response relative-to the 30:1 E:T ratio.

The memory CTL activity of mice inoculated with pCMV/VP7 was approximately 30% at an effector to target ratio of 60:1, compared to 45% lysis obtained with mice orally infected with EDIM rotavirus indicating an effective response to both the DNA vaccine and the EDIM virus. The low level of activity seen with the control DNA may be due to non-specific stimulation of natural killer cells by the plasmid vector. There was minimal lysis of uninfected target cells by the effector cells.

Example 4
Protective Immunity Against Homotypic Rotavirus Challenge Induced by Inoculation with the pCMVIA/VP7 Plasmid Initial experiments in mice inoculated with pCMV/VP7 did not show protection when challenged with EDIM virus strains EW at a concentration of $10^2$ adult $ID_{50}$/ml, even though the vaccine induced an immune response as determined by the presence of neutralizing serum antibody and CTL responses.

Figure 3:
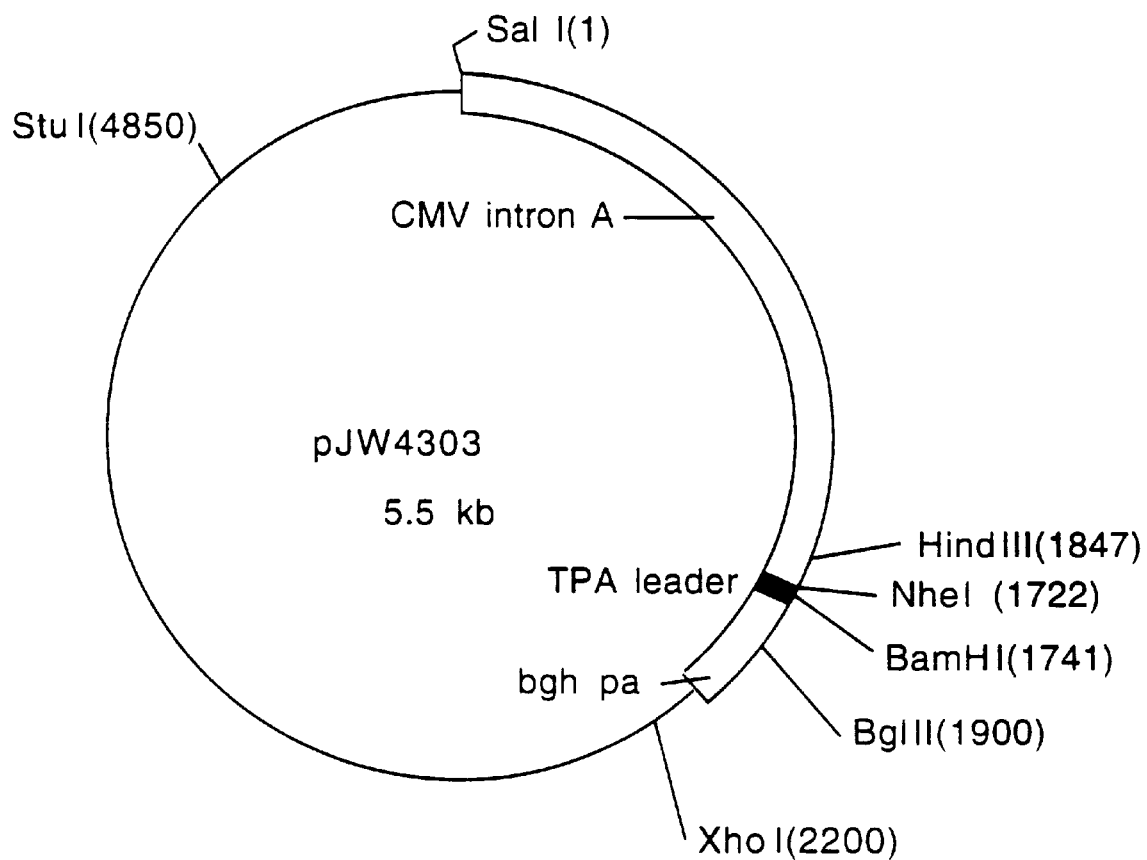
FIG. 3 is a schematic representation of the pJW4303 plasmid comprising the CMV intron A, a leader sequence for the tissue plasminogen activator (TPA) protein, and bovine growth hormone polyadenylation sequences.
Figure 4A:
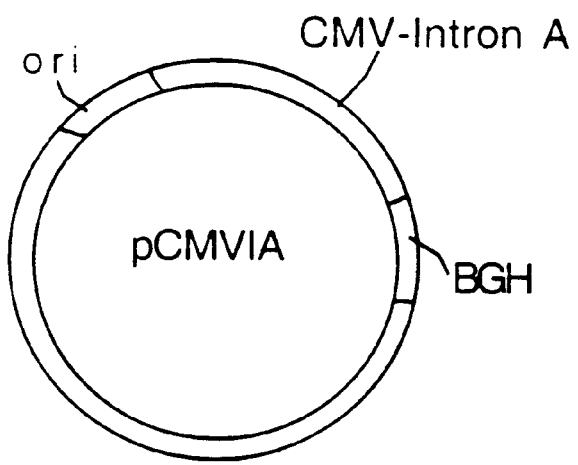
FIG. 4A is a schematic representation of control plasmid pCMVIA, a bacterial plasmid that includes the SV40 replication origin, the CMV immediate-early promoter/enhancer element, Intron A (the largest CMV intron), and a bovine growth hormone (BGH) gene that provides a polyadenylation signal. TPA is optionally removed for cloning purposes.
Figure 4B:
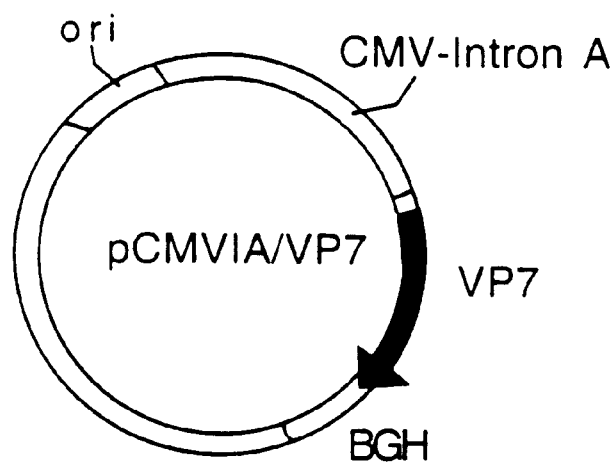
FIG. 4B is a schematic representation of the pCMVIA/VP7 plasmid, which includes the pCMVIA control plasmid and a rotavirus antigen DNA transcription unit encoding VP7 protein.

Surprisingly, protection by VP7 against homotypic rotavirus challenge as well as induction of antibody response was shown using a different plasmid vector, JW4303 shown in FIG. 3 (Dr. J. Mullins, University of Washington, Seattle, Wash. USA). The vector encodes a CMV promoter/enhancer element and also encodes intron A upstream of the rotavirus cDNA site of insertion. The presence of intron A (IA) positively regulates expression of the insert cDNA from the CMV immediate-early promoter/enhancer element in mammalian cell lines (Chapman, B. S., et al. (1991) Nucleic Acids Research 19:3979–3986). FIGS. 4A and 4B are diagrams showing the control plasmid (pCMVIA) and the plasmid containing a VP7 (SEQ ID NO:4) insert (pCMVIA/VP7). The bovine growth hormone (BGH) gene sequence provides polyadenylation signals necessary for expression.

The ability of the pCMVIA/VP7 DNA vaccine to provide protective immunity against homotypic virus challenge was demonstrated in the adult mouse model. Protection is determined by the quantitation of virus shedding in feces of inoculated mice following viral challenge.

Figure 5:
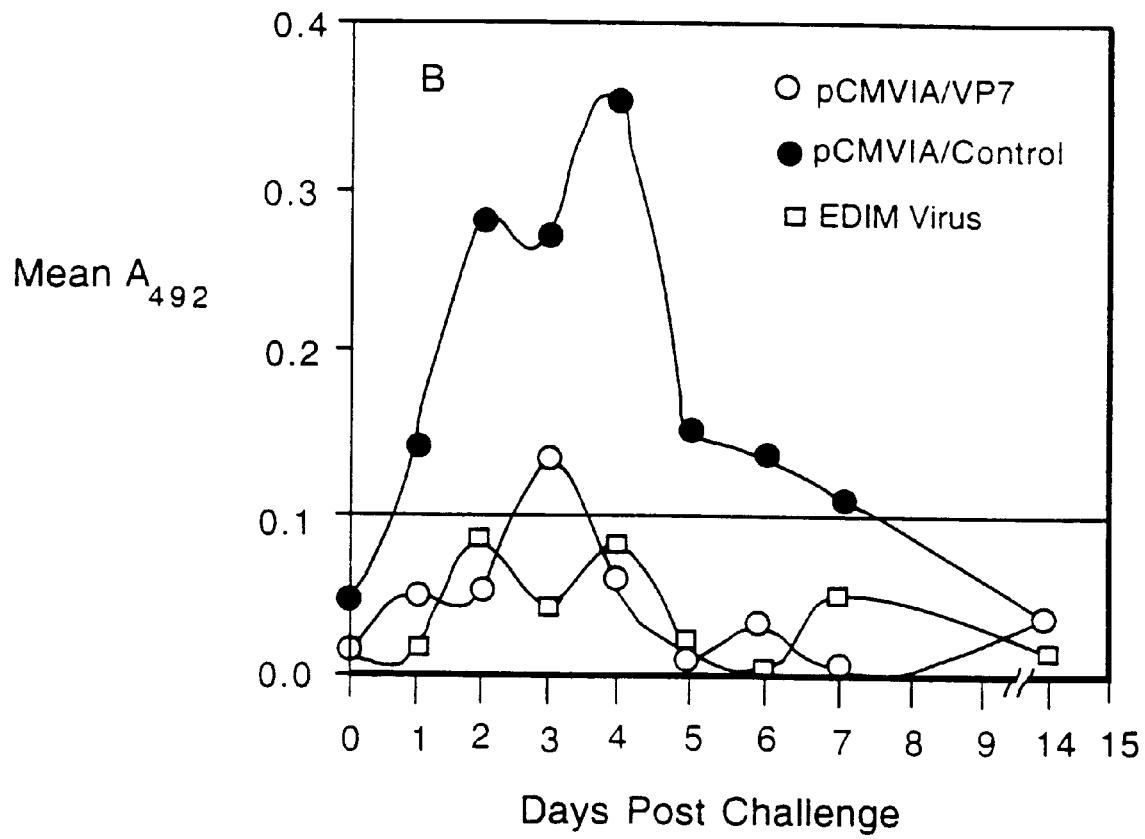
FIG. 5 is a graph showing protection against EDIM rotavirus challenge in immunized BALB/c mice. Mice were inoculated with pCMVIA/VP7, control plasmid pCMVIA, or had been infected with EDIM virus one month prior to challenge.

The results in FIG. 5 show that mice which received the control plasmid pCMVIA showed no protection against challenge virus (filled circles). Mice which received the pCMVIA/VP7 DNA vaccine (open circles; two inoculations at a 4 week interval) showed homotypic protection at 4 weeks following the second inoculation. This result is similar to that obtained in mice which had received a single oral inoculation with EDIM virus 4 weeks prior to analysis (open squares).

Example 5
Protective Immunity Against Homotypic Rotavirus Challenge Induced by Inoculation with the pCMVIA/VP4 DNA Vaccine The cDNA of murine strain EW rotavirus VP4 (SEQ ID NO:1; Dunn, S. J. et al. (1994) Virology 203:250–269; GenBank accession number U08429) was inserted into the pCMVIA plasmid between the BamHI and HindIII sites in the orientation for expression of the VP4 gene under the control of the CKV immediate-early promoter/enhancer element and the intron A sequence. Other sources of VP4 coding sequence include human rotavirus VP4 (Taniguchi, K. et al. (1988) J. Virol. 62:2421–2426; GenBank accession number M21014; FIG. 12; SEQ ID NO:5) and porcine rotavirus VP4 (Nishikawa, K. and Gorziglia, M. (1988) Nucl. Acids Res. 16:11847; GenBank accession number X13190).

Figure 6:
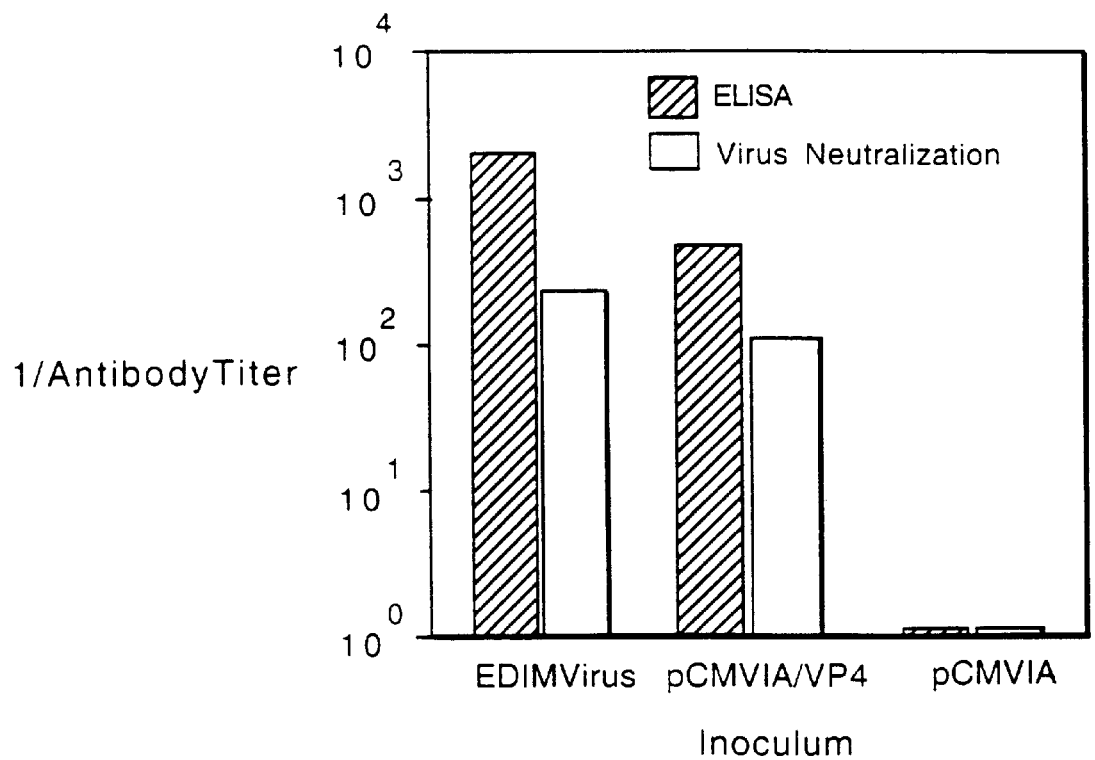
FIG. 6 is a bar graph showing the serum antibody responses to EDIM rotavirus in mice inoculated with the rotavirus itself, DNA vaccine pCMVIA/VP4, or control pCMVIA.

BALB/c ($H-2^d$) adult mice were inoculated with 0.4 μg of pCMVIA/VP4 DNA by gene gun delivery into the epidermis as was performed for the VP7 experiments above. For comparison, mice were inoculated with control plasmid vector or with live EDIM virus. Inoculated mice were tested for anti-VP4 antibodies in serum by the ELISA assay and rotavirus neutralizing antibodies in serum at 4 weeks following the second inoculation of plasmid or virus. The results shown in FIG. 6 indicate that EDIM virus and the pCMVIA/VP4 plasmid stimulated antibody responses, whereas no rotavirus-specific responses were seen in the mice inoculated with the plasmid control.

Figure 7:
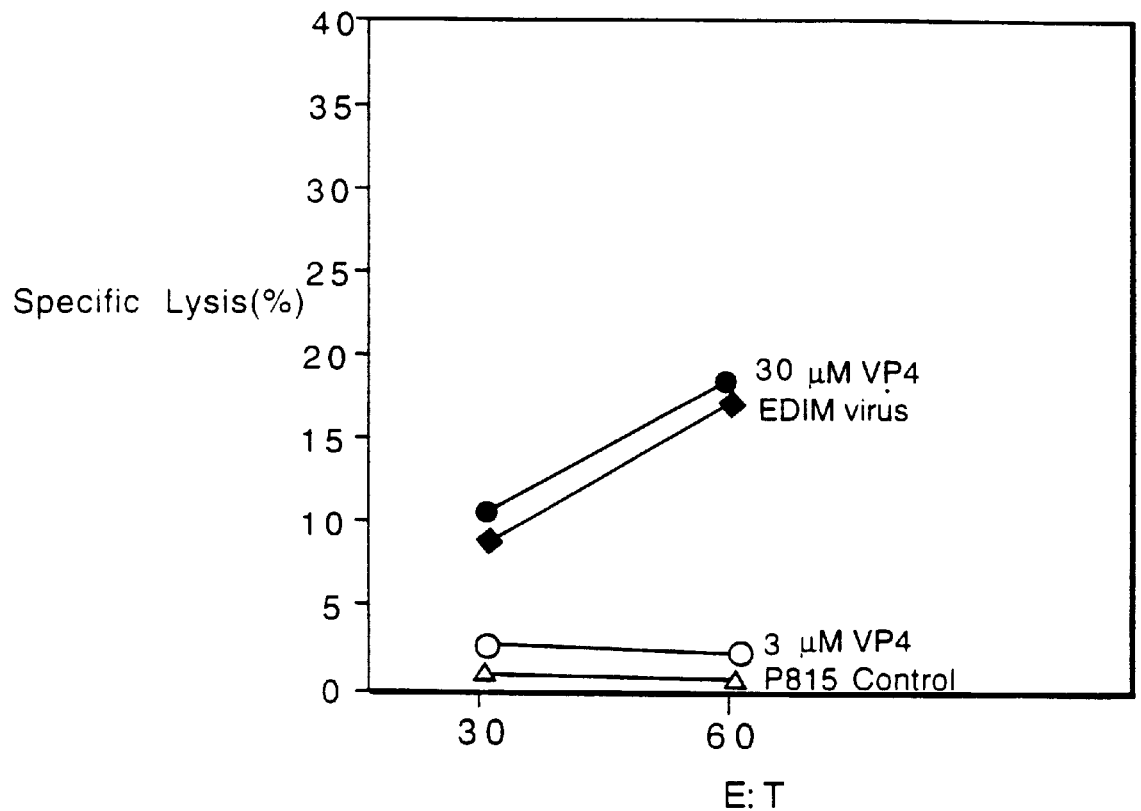
FIG. 7 is a graph showing the specificity of cytotoxic T cell (CTL) responses in pCMVIA/VP4-immunized BALB/c mice. Target cells (P815 cells) were infected with EDIM virus or coated with VP4 peptides at a concentration of 30 $\mu M/3 \times 10^6$ cells or 3 $\mu M/3 \times 10^6$ cells. The control cells were untreated P815 cells.

Cellular immune response was tested by examining memory CTL activity of splenic lymphocytes from pCMVIA/VP4 immunized mice. To test for VP4 specificity, P815 target cells were passively coated by incubation with VP4 peptides. The VP4 peptides were synthesized from a sequence published in Shimojo, N. et al. (1989) J. Immunol. 143:2939–2947, and prepared by the peptide synthesis facility at the University of Massachusetts Medical Center using standard synthetic techniques. The results of these assays are shown in FIG. 7. CTL activity of lymphocytes (effector cells) from mice inoculated with pCMVIA/VP4 was measured. The target cells were uninfected P815 target cells (open triangles), P815 target cells infected with EDIM virus (solid diamonds) or coated with VP4 peptide (at a concentration of 30 μM/3×10⁶ cells (solid circles) or 3 μM/3×10⁶ cells (open circles). The results show that inoculation of mice by DNA vaccine pCMVIA/VP4 produced cytotoxic activity against target cells infected with EDIM virus or coated with VP4 protein (at 30 μM VP4/3×10⁶ cell). There was essentially no cytotoxic activity against P815 control cells and cells coated with VP4 protein at 3 μM VP4/3×10⁶ cells. Providing another positive control, lymphocytes from mice infected with EDIM virus were found to exhibit CTL responses to the VP4-coated cells (data not shown).

Figure 8:
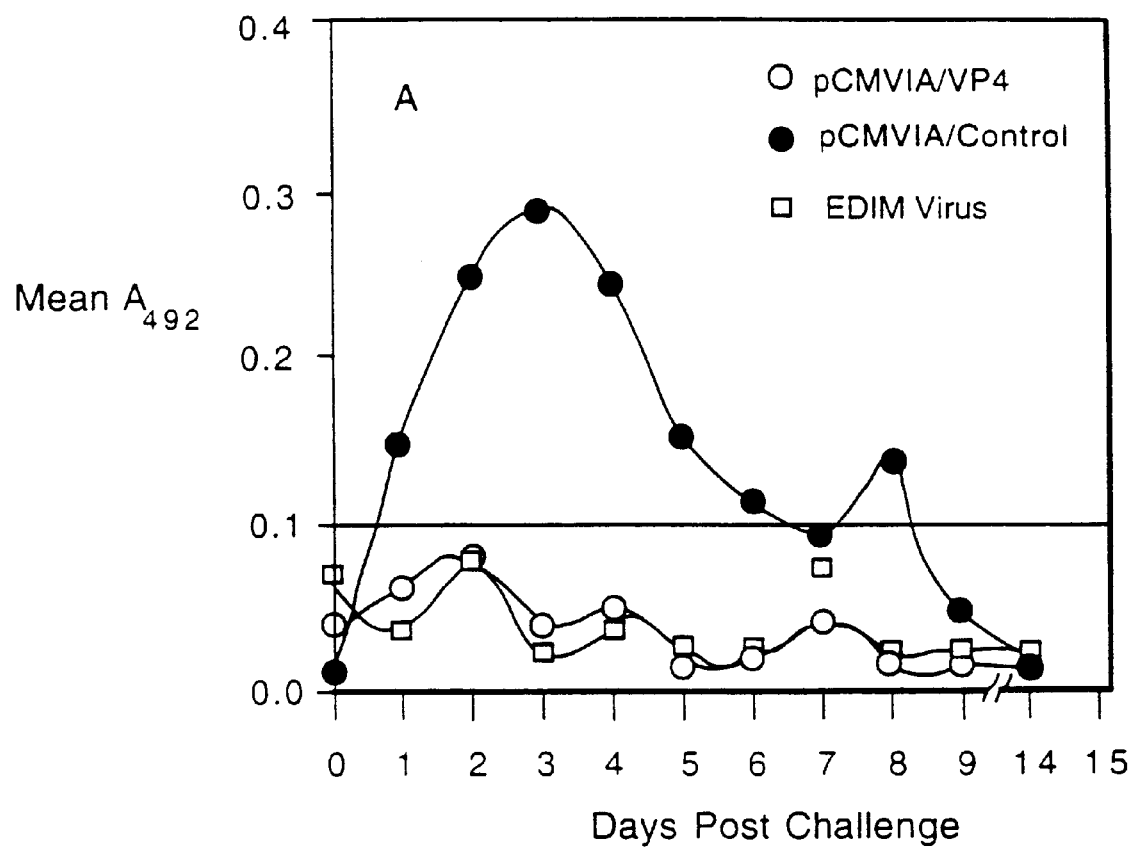
FIG. 8 is a graph showing protection against EDIM rotavirus challenge in immunized BALB/c mice. Mice were inoculated with pCMVIA/VP4, with control plasmid pCMVIA, or had been infected with EDIM virus one month prior to challenge.

The ability of the pCMVIA/VP4 DNA vaccine to provide protection against homotypic rotavirus challenge was demonstrated in adult mice by the same procedure as for VP7 in Example 4. The results showing the protective immunity against homotypic rotavirus infection induced by VP4 are shown in FIG. 8. Protection is measured by a reduction in virus shedding monitored by ELISA to be less than 0.1 $A_{492}$ units. Both the pCMVIA/VP4 DNA vaccine (open circles) and the live EDIM virus (open squares) provided protection against EDIM viral challenge as indicated by mean $A_{492}$ values less than 0.1 for 14 days post challenge. However, the pCMVIA control plasmid (filled circles) did not provide protection as indicated by $A_{492}$ values greater than 0.1 from 1 to 7 days post challenge.

Example 6
Protective Immunity Against Homotypic Rotavirus Challenge Induced by Inoculation with the pCMVIA/VP6 DNA Vaccine The cDNA of murine EDIM strain EW rotavirus VP6 cDNA (obtained from H. Greenberg, Stanford University, supra) was inserted into the pCMVIA plasmid between the BamHI and the HindIII in the orientation for expression of the VP6 gene under the control of the CMV immediate-early promoter/enhancer element and the intron A sequence. The cDNA encoding murine rotavirus VP6 coding sequence can be isolated by deriving probes and/or PCR primers from any of the following nucleotide sequences as well as other rotavirus VP6 sequences: human rotavirus VP6 (SEQ ID NO:2, Palombo, E. A. and Bishop, R. F. (1993), GenBank accession number U04741; FIG. 13); bovine rotavirus VP6 (SEQ ID NO:3, FIG. 14; Tarlow, 0. and McCrae, M. A. (1990) Nucl. Acids Res. 18:4921). Techniques for such isolation and/or PCR amplification are well known to those of ordinary skill in the art (see e.g., Sambrook, J. et al. *Molecular Cloning: A Laboratory Manual*, Cold Spring Harbor Laboratories (1989)).

Figure 9:
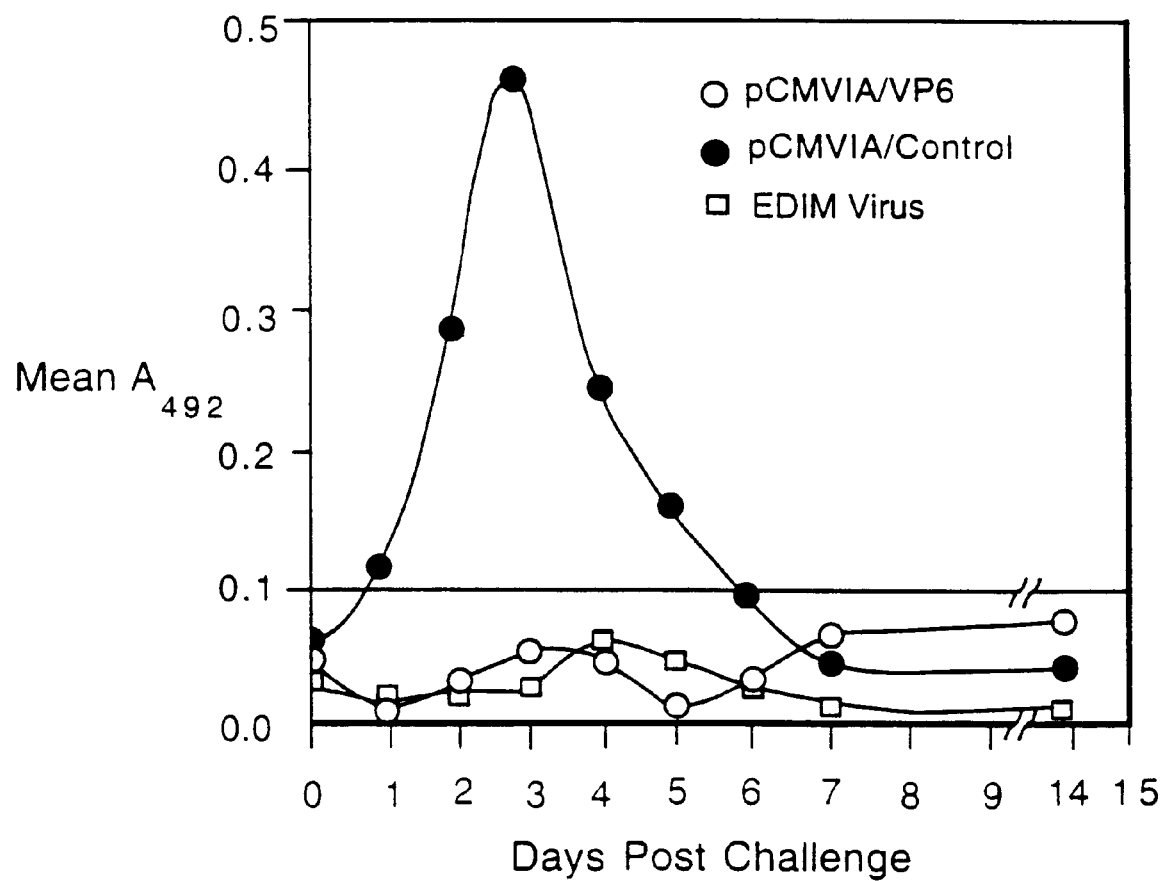
FIG. 9 is a graph showing protection against EDIM rotavirus challenge in immunized BALB/c mice. Mice were inoculated with pCMVIA/VP6, control plasmid pCMVIA, or had been infected with EDIM virus one month prior to challenge.

A pCMVIA plasmid containing a murine rotavirus gene encoding VP6, the internal rotavirus group antigen, demonstrated protective immunity against EDIM viral challenge using the same procedure used to test VP7 and VP4. A graph of pCMVIA/VP6-induced protective immunity to homotypic rotavirus challenge is shown in FIG. 9. Protection is measured by a reduction in virus shedding monitored by ELISA to be less than 0.1 $A_{492}$ units. Both the pCMVIA/VP6 DNA vaccine (open circles) and the live EDIM virus (open squares) provided protection against EDIM viral challenge as indicated by mean $A_{492}$ values less than 0.1 for 14 days post challenge. However, the pCMVIA control plasmid (filled circles) did not provide protection as indicated by $A_{492}$ values greater than 0.1 from 1 to 7 days post challenge. Thus, a similar degree of protection was obtained with the pCMVIA/VP6 DNA vaccine as seen for the VP4 and VP7 DNA vaccines.

This was a surprising result because the pCMVIA/VP6 construct did not elicit neutralizing antibodies and because protection by VP6 administration had not previously been shown. On the contrary, direct inoculation of VP6 had been shown not to be involved in protective immunity to EDIM challenge despite the apparent induction of antibody titers (Dormitzer, P. et al. Audio Tape (Aug. 10, 1993) IXth Intl. Congress of Virology, Workshop W21; Estes, M. K. and Cohen, J. (1989), Microbiol. Rev. 53:410–449; and Riepenhoff-Talty, M. et al. (1987) Adv. Exp. Med. Biol. 216B:1015–1023). Previously, both a VP6 and a recombinant VP7 ($VP7_{SC}$) encoded in a vaccinia virus or adenovirus vector did not elicit protective immunity (Audio Tape, Dormitzer, P. et al. (Aug. 10, 1993) IXth Intl. Congress of Virology, Workshop W21). The VP6 protein, expressed from pCMVIA/VP6 in a vertebrate cell, is shown for the first time to induce protective immunity to a rotavirus challenge even though no neutralizing antibodies were elicited. In fact, a DNA vaccine of the invention encoding a wild type inner core VP6 protein offers similar protection to the DNA vaccines encoding the outer capsid proteins VP4 or VP7 as described herein.

Example 7
Heterologous Immune Response Induced by pCMV/VP7 DNA Vaccine

Figure 10:
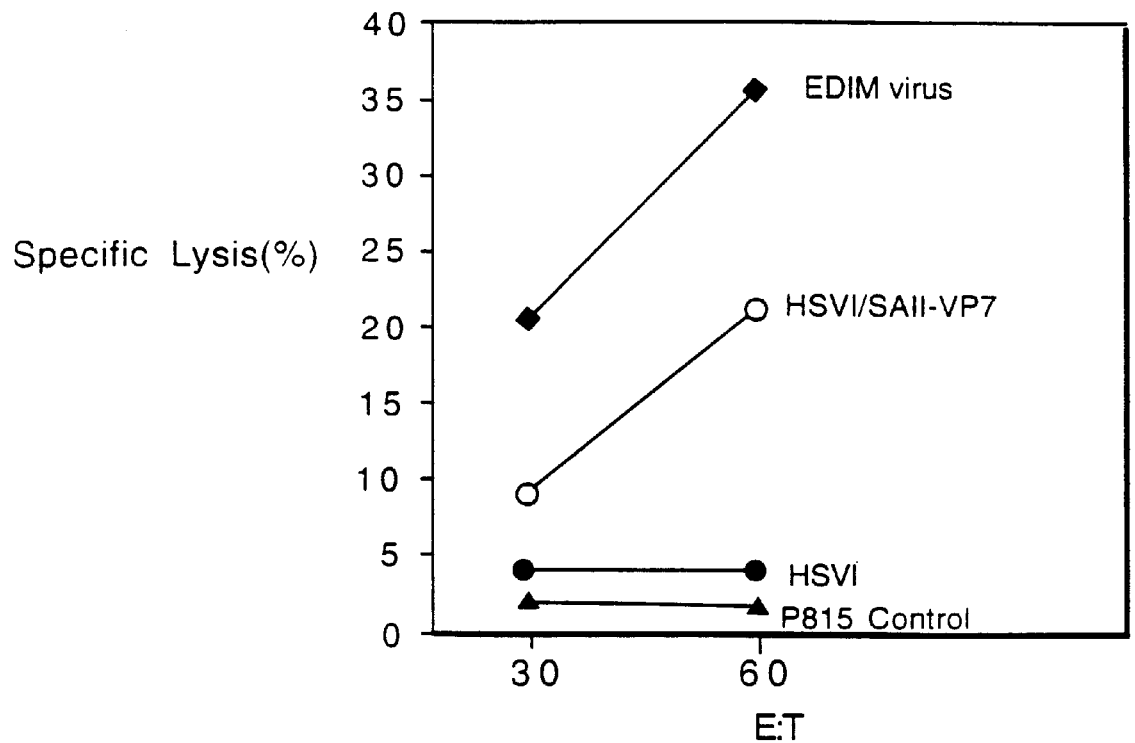
FIG. 10 is a graph showing the specificity of CTL responses in pCMV/VP7 immunized BALB/c mice. Target cells (P815 cells) were infected with EDIM virus (solid squares); HSVI encoding SAll rotavirus VP7 (open circles); or control HSVI (solid circles). The cell controls were untreated P815 cells (solid triangles).

The ability of EDIM strain EW-derived VP7 DNA vaccine to elicit an immune response to VP7 from rotaviruses of the same (homologous) or different (heterologous) species specificities was demonstrated. Target cells infected with EDIM strain EW virus (homologous test) or with herpes simplex virus (HSV) encoding simian (SA-11) rotavirus VP7 (Dormitzer, P. R. et al. (1994) Virology 204:391–402) (heterologous test) were tested for lysis by effector cells from mice inoculated with EDIM virus or with pCMV/VP7 DNA vaccine. The results are shown in FIG. 10. Lymphocytes from mice which had been inoculated with pCMV/VP7 showed CTL activity against P815 target cells infected with HSV expressing rotavirus strain SA-11 VP7 (open circles) as well as target cells infected with EDIM virus (closed squares). The percent specific lysis of target cells infected with EDIM virus or HSVI/SA-11 was approximately 35% and 20%, respectively, using effector cells from the pCMV/VP7 immunized mice at an E:T ratio of 60:1. Low background levels of CTL activity was observed against control P815 cells and P815 cells infected with HSV without a rotavirus encoded protein. Induction of CTL activity by pCMV/VP7 shows that the VP7 protein of one rotavirus serotype A strain can induce an immune response against the VP7 protein of another rotavirus serotype A strain.

Example 8
Heterotypic and Heterologous Protective Immunity Induced by pCMVIA/VP4, pCMVIA/VP6, and pCMVIA/VP7

Heterotypic protection by VP4, VP6, and VP7 is demonstrated by inoculating mice with a pCMVIA/VP4, pCMVIA/VP6, or pCMVIA/VP7 DNA vaccine by the procedure described in the examples above. Each of these DNA vaccines encodes a rotavirus protein derived from EDIM strain EW rotavirus. Following inoculation, the mice are challenged with a rotavirus strain which is heterologous or heterotypic relative to the rotavirus from which the VP4, VP6, or VP7 cDNA was derived.

Heterologous challenge is demonstrated by inoculating the mice with a DNA vaccine encoding VP4, VP6, or VP7 from a non-murine source (e.g., simian SA-11 or other non-murine rotavirus VP4, VP6, or VP7) followed by challenge with murine rotavirus by the procedures described in previous examples.

Following challenge, viral shedding is quantitated by ELISA and heterotypic protection is determined to be an ELISA value lower than 0.1 $A_{492}$ units. Control inoculation and homotypic challenge is performed in parallel to compare the relative degrees of protection.

The information gained by using an adult mouse model to assess vaccine effectiveness (as reduction in virus shedding) is a useful measure of effectiveness in larger vertebrates (Ward, R. L. et al. (1990) J. Virol. 64:5070–5075). Chronic viral shedding by adult cattle and swine is a reservoir for persistence of rotavirus between epidemics (Goto, Y. et al. (1986) Vet. Microbiol. 11:177–184; and Banfield, D. A. et al. (1982) J. Clin. Microbiol. 16:186–190) and is said to be true for humans (Offit, P. A. (1995) supra).

Example 9
A Method of Providing Protective Immunity Against Rotavirus in Swine

To provide protection against rotavirus infection in swine, a DNA vaccine encoding a porcine rotavirus protein is constructed. cDNA from a porcine rotavirus VP4 (Nishikawa and Gorziglia (1988), supra; GenBank accession number X13190), VP6 (Gonzalez, S. A. et al. (1995) J. Gen. Virol. 76:221–224), or VP7 (Gorziglia et al. (1988), supra; GenBank accession number X04613) is inserted in the pCMVIA plasmid as for the murine DNA vaccine constructs described above. Optionally, heterologous protection can be provided by administering a vaccine constructed using VP4, VP6, or VP7 from a rotavirus of different species specificity.

The DNA vaccine is administered to the animal by several routes selected from the following: intravenous, intramuscular, intraperitoneal, intradermal, inhalation, and subcutaneous administration. For example, intradermal administration by particle bombardment is a preferred route. The site of administration is chosen for the convenience of the administrator. Suckling pigs are inoculated by intradermal particle bombardment delivery of gold beads coated with the pCMVIA plasmid vector containing VP4, VP6, or VP7 cDNA from porcine or other species-specific rotavirus strains. The dose is between 1 and 50 μg of DNA vaccine per kg body weight of the pig, preferably 10–25 μg per kg body weight. Inoculations are given at 4 week intervals until the animal is provided with long term cellular immune response.

Protection is determined by challenging the inoculated pigs with porcine rotavirus from the same serotype and the same or different strain. Virus shedding is monitored by standard techniques known to those of ordinary skill in the art and disease symptoms such as diarrhea are monitored relative to an uninoculated pig.

Example 10
A Method of Providing Protective Immunity Against Rotavirus in Humans Rotavirus serogroups A, B, and C are known to cause severe gastroenteritis in humans. Human infants (from 6 to 24 months of age), adults parenting infected infants, elderly humans, and immunocompromised humans of any age are susceptible to developing disease upon infection with rotavirus. To provide protection in humans against rotavirus infection, a DNA vaccine encoding a human rotavirus protein is constructed. cDNA from the human rotavirus VP4 (Taniguchi, (1988), supra; GenBank accession number M21014; FIG. 12), VP6 (SEQ ID NO:2; FIG. 13), or VP7 (Dyall-Smith, M. L., WO 8901514-A; GenBank accession number A01321; FIG. 16; SEQ ID NO:6) is inserted in the pCMVIA plasmid as for the murine DNA vaccine constructs described above. optionally, heterologous protection can be provided by administering a vaccine constructed using VP4, VP6, or VP7 from a rotavirus of different species specificity.

Administration of a DNA vaccine to a human can be performed by any one or more of several routes selected from the following: intravenous, intramuscular, intraperitoneal, intradermal, inhalation, and subcutaneous. For example, intradermal administration by gene gun is a preferred route. The site of administration is chosen for the convenience of the patient. A human patient is inoculated with the human rotavirus-derived pCMVIA/VP4, pCMVIA/VP6, or pCMVIA/VP7 DNA vaccine by gene gun delivery of DNA-coated gold beads. The dose is between 1 and 50 μg of DNA vaccine per kg body weight, preferably 10–25 μg per kg body weight. For a human infant, two inoculations are given at a 4 week interval. A human of any age who is caring for an infected infant or is immunocompromised due to illness, drug treatment, or other cause putting him or her at risk of rotavirus infection is inoculated with the DNA vaccine by gene gun delivery for at least 2 inoculations at 4 week intervals.

Mucosal routes of DNA inoculation involve the administration of microsphere-encapsulated DNA to raise protective responses against a rotavirus challenge. pCMVIA/VP4, pCMVIA/VP6, or pCMVIA/VP7 DNA can be encapsulated in microspheres. Each patient receives a primary inoculation and a boost. The patients receive approximately 1–50 μg/kg body weight of microsphere-encapsulated DNA for both the primary and boost inoculations. Each administration of encapsulated DNA is delivered in 100 μl of water intranasally.

Use

Rotavirus disease in human infants and adults occurs worldwide and is responsible for the hospitalization and even the death of many patients. Disease caused by rotavirus in animals, such as pigs, results in significant losses in agricultural revenue each year. Thus, a safe, effective vaccine that protects against infection by rotavirus is important in both human and verterinary medicine.

A human rotavirus DNA vaccine of the invention is useful in providing protection against rotavirus infection in human infants, caretakers of infected infants, and immunocompromised humans. A porcine DNA vaccine of the invention is useful to prevent rotavirus infection in piglets thereby allowing the animals to thrive for increased agricultural benefit. A DNA vaccine against any human or animal rotavirus can be constructed and used according to the invention. Such vaccines are useful in providing homologous protection against a specific strain of rotavirus. The DNA vaccine of the invention is also useful in providing heterologous protection in that a DNA vaccine derived from one species-specific rotavirus, serotype, or strain can be used to induce protective immunity against a rotavirus from a different species-specific rotavirus, serotype, or strain.

Broad protection against multiple strains within a given serotype is possible according to the invention by inoculating the human or animal with a DNA vaccine encoding a protection-inducing protein from a rotavirus strain of the same serotype. Thus, a single DNA vaccine of the invention is useful in providing protection against multiple strains of rotavirus (see Example 8, above).

The DNA vaccine of the invention is also useful for diagnosis of rotavirus infection. Virus particles from stool of the patient or infected animal are contacted with serum of an animal, such as a mouse, which has been inoculated with a known serotype, species-specific DNA vaccine of the invention. Viral neutralization by the serum antibodies or other type-specific assays informs the clinician as to the disease-causing rotavirus serotype.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method of eliciting an immune response against a rotavirus in a vertebrate, said method comprising administrating to the vertebrate a plasmid vector comprising one or more isolated nucleotide sequences each encoding a rotavirus polypeptide selected from the group consisting of VP4, VP6, and VP7, and transcriptional and translational regulatory sequences operably linked to the isolated nucleotide sequences, whereby expression of said nucleotide sequences in one or more cells in the vertebrate elicits a humoral immune response, a cell-mediated immune response, or both, against the rotavirus.

2. A method of eliciting a protective immunity against a rotavirus infection in a vertebrate, said method comprising administering to the vertebrate a plasmid vector comprising one or more isolated nucleotide sequence each encoding a rotavirus polypeptide selected from the group consisting of VP4, VP6, and VP7, and transcriptional and translational regulatory sequences operably linked to the isolated nucleotide sequences, whereby expression of said nucleotide sequences in one or more cells in the vertebrate elicits a humoral immune response, a cell-mediated immune response, or both against the rotavirus in the vertebrate, and whereby the vertebrate is protected from the disease caused by subsequent exposure to the rotavirus.

3. A method of claim 2, wherein the regulatory sequences are of nonretroviral origin.

4. A method of claim 2, wherein at least one of said regulatory sequences is the cytomegalovirus immediate-early enhancer promoter.

5. A method of claim 2, wherein at least one of said regulatory sequences is intron A.

6. A method of claim 2, wherein said rotavirus polypeptide is VP4.

7. A method of claim 2, wherein said rotavirus polypeptide is VP6.

8. A method of claim 2, wherein said rotavirus polypeptide is VP7.

9. A method of claim 2, wherein said vertebrate is a pig.

10. A method of claim 2, wherein said vertebrate is a human.

11. A method of claim 2, wherein the plasmid vector is administered to the vertebrate through a route of administration selected from the group consisting of inhalation, intravenous, intramuscular, intraperitoneal, intradermal, and subcutaneous.

12. A method of claim 2, wherein the plasmid vector is administered to the vertebrate by contacting the plasmid vector with a mucosal surface of the vertebrate.

13. A method of claim 2, wherein the plasmid vector is micorosphere encapsulated, and is administered to the vertebrate by contacting the microsphere-encapsulated plasmid vector with a mucosal surface of the vertebrate.

14. A method of claim 2, wherein the plasmid vector is coated onto gold beads for administration to the vertebrate by particle bombardment delivery.

15. A method of claim 14, wherein the gold beads are approximately 1 $\mu$m to 2 $\mu$m in diameter.

16. A method of claim 2, wherein the protective immunity is homologous, homotypic, heterotypic, or heterologous.

17. A method of claim 2, wherein the vertebrate is a mammal.

* * * * *